United States Patent [19]

Olofson et al.

[11] Patent Number: 4,772,695

[45] Date of Patent: Sep. 20, 1988

[54] PROCESS FOR THE PREPARATION OF VINYL CARBAMATES

[75] Inventors: Roy A. Olofson; Gary P. Wooden, both of State College; Jonathan T. Martz, Pittsburgh, all of Pa.

[73] Assignee: Societe Nationale des Poudres et Explosifs, Paris, France

[21] Appl. No.: 533,630

[22] Filed: Sep. 19, 1983

Related U.S. Application Data

[63] Continuation-in-part of Ser. No. 423,465, Sep. 24, 1982, abandoned.

[51] Int. Cl.$^4$ ............................................. C07D 273/08
[52] U.S. Cl. ............................ 540/467; 544/172; 544/388; 544/389; 546/130; 546/189; 546/226; 546/245; 546/321; 548/261; 548/262; 560/24; 560/30; 560/115; 560/158; 560/161; 560/167; 560/168; 560/213; 585/642; 585/657; 260/696
[58] Field of Search ............... 544/172, 388, 389; 546/245, 130, 189, 226, 321; 548/261, 262; 560/24, 30, 115, 158, 161, 167, 168, 213; 260/696; 585/642, 657; 540/467

[56] References Cited

U.S. PATENT DOCUMENTS

| | | | |
|---|---|---|---|
| 1,934,613 | 11/1933 | Jacobi et al. | 560/213 |
| 2,087,466 | 7/1937 | Bauer et al. | 560/213 |
| 2,111,509 | 3/1938 | Loder | 560/213 |
| 2,210,564 | 8/1940 | Andrussow et al. | 560/213 |
| 2,245,547 | 6/1941 | Pollack | 560/213 |
| 2,673,875 | 3/1954 | Anspon | 560/213 |
| 3,652,608 | 3/1972 | Fenton | 560/213 |
| 3,718,684 | 2/1973 | Pande et al. | 560/213 |
| 4,072,687 | 2/1978 | Togo et al. | 560/213 |
| 4,442,301 | 4/1984 | Gozzo et al. | 560/213 |
| 4,604,482 | 8/1986 | Ohmori et al. | 560/213 |

OTHER PUBLICATIONS

Lucas, *Organic Chemistry*, Sec. Ed., 1953, American Book Co., N.Y., pp. 60–61, 65, 112–115.

*Primary Examiner*—Glennon H. Hollrah
*Assistant Examiner*—James H. Turnipseed
*Attorney, Agent, or Firm*—Bucknam and Archer

[57] ABSTRACT

A process for the preparation of vinyl carbamates of formula I

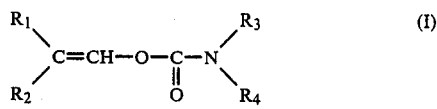

is described which comprises heating an α-halogenocarbamate of formula II

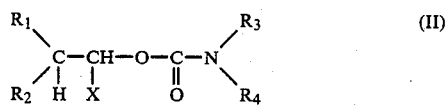

in which X is a halogen atom at a temperature between 70° and 250° C. for a period of time between several minutes up to several hours. $R_1$, $R_2$, $R_3$, and $R_4$ are the same or different. The process is applicable to a great variety of products in which $R_1$, $R_2$, $R_3$, and $R_4$ have different meanings. The process permits to prepare in a simple and economical fashion, vinyl carbamates, which have industrial value and novel vinyl carbamates.

7 Claims, No Drawings

PROCESS FOR THE PREPARATION OF VINYL CARBAMATES

This application is a continuation-in-part of U.S. Ser. No. 423,465 filed Sept. 24, 1982 now abandoned.

The present invention relates to a novel process for the preparation of vinyl carbamates. This invention also relates to novel vinyl carbamates, which are valuable as agricultural pesticides, herbicides, insecticides and related materials, intermediates in the preparation of valuable pharmaceuticals and which by polymerization lead to valuable substances.

Within the last 25 years, several processes of preparation of vinyl carbamates have been reported in the literature. According to French Patent No. 1,478,633 to Dow Chemical Company, some N-heterocyclic vinyl carbamates have been prepared by reaction of a vinyl haloformate and an N-heterocyclic secondary amine. However, the vinyl haloformates starting materials are substances very difficult to prepare. For instance, the process described in the U.S. Pat. No. 2,377,085, which consists of pyrolyzing bis-glycol chloroformate at 450° C. does not permit to obtain more than 11% of vinyl chloroformate. Schaefgen in U.S. Pat. No. 3,118,862 and Lee in the Journal of Organic Chemistry, Volume 30, page 3943, (1965) have improved this synthesis, but the improvements only give 30 and 44% yield respectively. One difficulty is that the tubular reactors become plugged. Another difficulty is that the by-products are toxic and carcinogenic. A new process has been developed in the laboratories of Societe Nationale des Poudres et Explosifs according to which phosgene is reacted with a salt of mercury. This process is described in U.S. Pat. No. 4,210,598. The process permits to obtain the vinyl chloroformates in better yield and utilize them for the preparation of the carbamates on a large scale. Even this process though, presents some drawbacks, mainly in the use of the mercury salts, which are expensive and which require particular precautions.

Another process of preparation of vinyl carbamates consists of dehydrohalogenating β-chloroethyl carbamates. This process is described in Journal of Organic Chemistry, Vol. 27, p. 4331 (1962). The yields are low and several by-products are obtained. The dehydrohalogenation only occurs in the presence of potassium tertiary butoxide, which is an expensive reagent and also difficult to handle. This process therefore, may be used on an industrial scale only with difficulty.

In the Journal Chemistry and Industry, in the issue of Feb. 8, 1969, page 166, Franko-Filipasic and Patarcity reported that they obtained by reaction of a few ketones and one aldehyde with dialkylcarbamoyl chlorides, some vinyl carbamates with equally low yields. These investigators formulated the hypothesis that an intermediate such as an α-chloroalkyl carbamate is formed and rapidly dehydrohalogenated, but they did not detect even a trace of this intermediate and did not succeed in increasing the rate of reaction by addition of several catalysts. Olofson and Cuomo, Tetrahedron Lett. 21 819 (1980) reported the synthesis of N-(E,Z-propenyloxycarbonyl)morpholine through a fluorocarbamate by reaction with a trimethyl silyl ether, which is an expensive reagent.

Recently, Stang and Anderson in the Journal of Organic Chemistry, Vol. 46, p. 4585, (1981) reported that they again attempted to prepare vinyl carbamates, but using a new route, that is using the isocyanates through the intermediate carbenes. This synthesis also has drawbacks because it requires a fluoride, which is a laboratory reagent, very expensive and not suitable for large scale operations. Further, only a few milligrams of the desired product were obtained.

The foregoing summary demonstrates that there has been a need at least within the last twenty-five years of a process of preparation of vinyl carbamates, which is simple, economical and which is utilizable on an industrial scale. There has also been a need of novel vinyl carbamates.

One object of the present invention is to prepare vinyl carbamates by a simple and economical process suitable on an industrial scale and which gives the desired products in good yields.

Another object of the present invention is to prepare novel vinyl carbamates, which have value as fragrances, pesticides and monomers and also known carbamates which after polymerization have value as moldable substances as described in French Patent No. 1,478,633 and Journal of Organic Chemistry, Vol. 27, p. 4331, (1962).

More specifically, the present invention covers a process for the preparation of vinyl carbamates of formula I

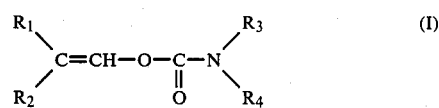

in which $R_1$ and $R_2$ are the same or different and are:
hydrogen;
a saturated or unsaturated, substituted or unsubstituted, aliphatic, cycloaliphatic, or heterocyclic radical;
a substituted or unsubstituted aromatic radical;
a group such as

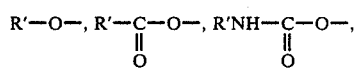

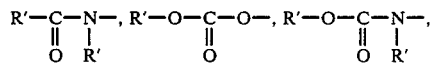

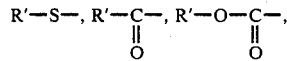

in which R' is a hydrocarbon radical;
a halogen atom, preferably chlorine or fluorine;
or $R_1$ and $R_2$ together with the carbon atom to which they are attached form a ring, which may be saturated or unsaturated, substituted or unsubstituted;

The symbols $R_3$ and $R_4$ in the formula I hereinabove, may be the same or different and may vary widely since they are far from the reaction center. They may be for instance,
hydrogen;
a substituted or unsubstituted, saturated or unsaturated aliphatic radical, cycloaliphatic or heterocyclic, the unsaturation, however, being on a carbon atom, which is not adjacent to the nitrogen atom;
a chain which comprises carbon atoms and at least another heteroatom;
a chain which comprises carbon atoms and at least another vinyl carbamate group;

a chain which comprises carbon atoms and at least another heteroatom and at least another vinyl carbamate group;

a substituted or unsubstituted aromatic radical;

or $R_3$ and $R_4$ form with the nitrogen to which they are attached, a heterocyclic ring, which may be saturated or unsaturated, substituted or unsubstituted, and which may be part of a condensed ring structure and which may contain at least another (a) heteroatom which may be O, S, N—$R_x$, wherein $R_x$ is a hydrocarbon radical, and/or (b) nitrogen atom which forms a vinylcarbamate group.

It should be noted that $R_3$ and $R_4$ may include keto groups, esters of primary, secondary and tertiary alcohols and of methanol, conjugated esters, ethers including aromatic ethers and amide functional groups. They may also include quaternary ammonium salts.

According to a specific embodiment, $R_1$ and $R_2$ are the same or different and are:

hydrogen;

a saturated or unsaturated, substituted or unsubstituted, aliphatic radical;

$R_1$ and $R_2$ together with the carbon atom to which they are attached form a ring which is saturated or unsaturated, substituted or unsubstituted;

$R_3$ and $R_4$ are the same or different and are:

hydrogen;

a substituted or unsubstituted, saturated or unsaturated, aliphatic, cycloaliphatic or heterocyclic radical, the unsaturation being on a carbon atom, which is not adjacent to the nitrogen atom;

a radical of formula $$-Z-N-C-O-CH=C\begin{matrix}R_1\\ \\R_2\end{matrix}$$
$$\phantom{-Z-N}|\phantom{-C}\|$$
$$\phantom{-Z-N}Y\phantom{-}O$$

wherein Z=a chain with 2 to 6 carbon atoms, Y=alkyl, and $R_1$ and $R_2$ are again as defined herein above;

a substituted or unsubstituted aromatic radical;

$R_3$ and $R_4$ form together with the nitrogen atom to which they are attached, a heterocyclic ring;

$R_3$ and $R_4$ form together with the nitrogen atom to which they are attached, a heterocyclic ring, which is part of a condensed ring structure;

$R_3$ and $R_4$ form together with the nitrogen atom to which they are attached a heterocyclic ring which contains at least another heteroatom;

$R_3$ and $R_4$ form with the nitrogen atom to which they are attached a heterocyclic ring which contains at least one oxygen atom and at least one additional nitrogen atom;

$R_3$ and $R_4$ together with the nitrogen atom to which they are attached form a piperazine ring and both nitrogen atoms of the piperazine ring have attached said group of formula:

$$\begin{matrix}R_1\\ \\R_2\end{matrix}C=CH-O-\overset{\displaystyle O}{\underset{\|}{C}}-$$

The process for the preparation of the vinyl carbamates according to formula I hereinabove according to the present invention comprises heating an o-halogeno carbamate of formula II:

$$\begin{matrix}R_1\\ \\R_2\end{matrix}C-CH-O-C-N\begin{matrix}R_3\\ \\R_4\end{matrix}\quad (II)$$
$$\phantom{xxx}|\phantom{x}|\phantom{xx}\|$$
$$\phantom{xxx}H\phantom{x}X\phantom{xx}O$$

in which $R_1$, $R_2$, $R_3$ and $R_4$ have the same meaning as defined hereinabove and X is a halogen atom, at a temperature between 70° and 250° C. for a period of time between several minutes up to several hours whereby a halohydric acid is formed and isolating the carbamate of formula (I) from the reaction mixture. The process according to the present invention, therefore, may be represented by the equation hereinbelow:

$$\begin{matrix}R_1\\ \\R_2\end{matrix}C-CH-O-C-N\begin{matrix}R_3\\ \\R_4\end{matrix}\longrightarrow$$
$$\phantom{xxx}|\phantom{x}|\phantom{xx}\|$$
$$\phantom{xxx}H\phantom{x}X\phantom{xx}O$$

$$\begin{matrix}R_1\\ \\R_2\end{matrix}C=CH-O-C-N\begin{matrix}R_3\\ \\R_4\end{matrix}+HX$$
$$\phantom{xxxxxxxx}\|$$
$$\phantom{xxxxxxxx}O$$

As shown in the equation hereinabove, the process according to the present invention permits to use as starting material substances which are easy to prepare and an apparatus, which is not very complex nor very expensive and permits to obtain the vinyl carbamates with a good yield and without by-products, which would be difficult to separate and difficult to remove.

The present invention also covers novel vinyl carbamates, which are valuable industrial products, which may be represented by the formula hereinbelow:

$$\begin{matrix}R_1'\\ \\R_2'\end{matrix}C=CH-O-C-N\begin{matrix}R_3'\\ \\R_4'\end{matrix}\quad (III)$$
$$\phantom{xxxxxxxx}\|$$
$$\phantom{xxxxxxxx}O$$

wherein $R_1'$ and $R_2'$ are the same or different and are:

hydrogen;

a saturated or unsaturated, substituted or unsubstituted, aliphatic, cycloaliphatic, or heterocyclic radical;

a substituted or unsubstituted aromatic radical;

a group such as $$R'-O-,\ R'-\underset{\underset{O}{\|}}{C}-O-,\ R'NH-\underset{\underset{O}{\|}}{C}-O-,$$

$$R'-\underset{\underset{O}{\|}}{C}-\underset{R'}{\overset{}{N}}-,\ R'-O-\underset{\underset{O}{\|}}{C}-O-,\ R'-O-\underset{\underset{O}{\|}}{C}-\underset{R'}{\overset{}{N}}-,$$

$$R'-S-,\ R'-\underset{\underset{O}{\|}}{C}-,\ R'-O-\underset{\underset{O}{\|}}{C}-,$$

in which R' is a hydrocarbon radical;

a halogen atom;

or $R_1'$ and $R_2'$ together with the carbon atom to which they are attached form a ring, which may be saturated or unsaturated, substituted or unsubstituted;

$R_4'$ is:

hydrogen;

a substituted or unsubstituted, saturated or unsaturated, aliphatic, cycloaliphatic or heterocyclic radical, the unsaturation being on a carbon atom, which is not adjacent to the nitrogen atom;

a chain which comprises carbon atoms and at least another heteroatom;

a chain which comprises carbon atoms and at least another vinylcarbamate group;

a chain which comprises carbon atoms and at least another heteroatom and at least another vinylcarbamate group;

or a substituted or unsubstituted aromatic radical;

when $R_3'$ has the formula (IV)

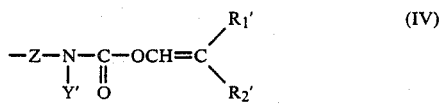

in which $R_1'$ and $R_2'$ are identical or different and are the same as defined hereinabove, y' is the same as $R_4'$ and Z is:

(a) a hydrocarbon chain consisting of 2-20 carbon atoms or (b) a hydrocarbon chain of 2 to 20 carbon atoms additionally containing heteroatoms, W, in which W is O, S, NR", each heteroatom being separated from another heretoatom by at least two carbon atoms and R" is a hydrocarbon radical;

(c) Z is a radical $-(CH_2)_nOCOO(CH_2)_n$ and n is an integer number between 2 and 10;

or $R_3'$ and $R_4'$ form together with the N to which they are attached

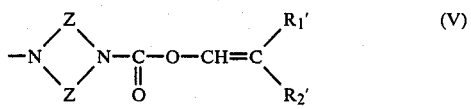

in which Z, $R_1'$ and $R_2'$ have the same meaning as hereinabove or $R_3'$ and $R_4'$ form together with the N to which they are attached together with the N to which they are attached a ring of formula (VI)

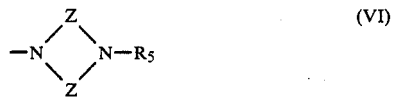

or R'4 is an aliphatic radical of 1 to 12 carbon atoms, preferably 1 to 4 carbon atoms, when R'3 is an aliphatic radical of 2 to 12 carbon atoms, preferably 2 to 10 carbon atoms, which radical ends with a quaternary ammoniun salt or $R_1'$ is hydrogen when $R_2'$ has a cyclic structure or is an aliphatic unsaturated radical substituted by chlorine, and when $R_3'$ is hydrogen or alkyl of 1 to 4 carbon atoms and $R_4'$ is alkyl of 1 to 4 carbon atoms;

wherein Z has the same meaning as hereinabove and $R_5$ is a hydrocarbon radical; and $R_4'$ ; alkyl of 1 to 4 carbon atoms; or R'4 is an aliphatic radical of 1 to 12 carbon atoms, preferably 1 to 4 Carbon atoms, when R'3 is an aliphatic radical of 2 to 12 carbon atoms, preferably 2 to 10 carbon atoms, which radical ends with a quaternary ammonium salt or $R_1'$ is hydrogen when $R_2'$ has a cyclic structu-e or is an aliphatic unsaturated radical substituted by chlorine, and when $R_3'$ is hydrogen or alkyl of 1 to 4 carbon atoms and $R_4'$ is alkyl of 1 to 40 carbon atoms.

The novel vinyl carbamates of formula III obtained according to the process of the present application are particularly valuable when they have the formula (VII)

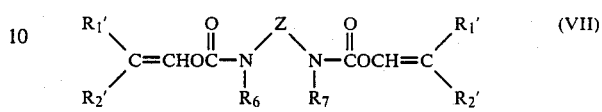

wherein $R_1'$ and $R_2'$ may be the same or different and are the same as hereinabove;

Z is an alkylene chain from 2 to 20 carbon atoms or a chain of carbon atoms and heteroatoms, W, in which W is O, S, NR" and W may be the same or different and R" is a hydrocarbon radical, each heteroatom being separated from another heteroatom by at least two carbon atoms;

$R_6$ and $R_7$ may be the same or different and have the same meaning as $R_3$ and $R_4$ in formula (I) or together may be the same as Z thus forming a cyclic structure.

With reference to formula III, particularly valuable are the compounds in which (a) $R_4'$ is alkyl and Z is a chain which contains between 2 and 10 carbon atoms, some of which may be replaced by heteroatoms, such as oxygen, provided that there are at least two carbon atoms between each heteroatom. Preferably, the valuable vinyl carbamates are those which have a chain Z containing between 2 and 6 carbon atoms or carbon and in which n is 1, 2, or 3 and $R_8$ is a hydrocarbon radical or another VOC radical.

$R_x$, $R_5$, R", and $R_8$ may be the same and are preferably hydrocarbon radicals of 1 to 10 carbon atoms.

One substantial advantage of the present invention is that it makes available novel compounds, which up to now have been inaccessible and which have value as agricultural pesticides, herbicides, insecticides, and related materiais. Another advantage is that they contain a carbon-carbon double bond, which may be used to carry out additional reactions with a variety of different compounds. Finally, in view of the presence of the double bond, they may be polymerized to prepare novel compounds, such as organic plastic materials with properties similar to glass.

The invention is described hereinbelow in more detail. With reference to formula II, which defines the carbamate starting material, X is preferably chlorine or bromine so that the compounds, which are being dehydrohalogenated are preferably α-chloro-carbamate or α-bromocarbamate. For the preparation of the α-halogenocompounds, it is possible to use the process of U.S. Ser. No. 280,241 filed on July 6, 1981 in the name of T. Malfroot, M. Piteau, and J. P. Senet, which permits to use readily available tertiary amines and α-halochloroformates as the starting materials. They may also be prepared by reaction of the same α-halogenated chloroformates with ammonia, primary amines or secondary amines in the presence of a substance, which acts as the acceptor of the halohydric acid formed.

The α-chlorochloroformate may be prepared by photochemical chlorination of the corresponding chloroformates or much better, by reaction of phosgene with an aldehyde in the presence of a catalyst as described in European patent No. 40153.

According to one embodiment of the invention, one adds to the reaction medium, at least one catalyst, which is a salt, capable of ionizing easily, the anion of which is not nucleophilic or is only weakly nucleophilic. The cation may be a metallic cation and preferably it is an alkali or alkaline earth metal cation. Advantageously, the metal cation is associated in the form of a complex such as a crown-ether or a cryptate. The cation may also be an organic cation. It is preferably one of the oniums such as ammonium, phosphonium, arsonium, sulfonium, and particularly the onium cations which are substituted by at least one radical and usually more than one radical having at least four carbon atoms. The quaternaryammonium ions are the preferred cations.

The anion is a halide, preferably chloride, bromide, or another anion which is non-nucleophilic or only weakly nucleophilic, such as for instance, $ClO_4^-$ or $NO_3^-$.

It is possible to utilize as a catalyst, the chloride of lithium, sodium, potassium, magnesium, and calcium and also lithium bromide and potassium fluoride. Potassium chloride associated with 18-crown-6 or 2,2,2-cryptate gives very good results. The quaternary ammonium halides are among the preferred catalysts. One may cite benzyl tributylammonium chloride or bromide, tetrahexyammonium chloride or bromide and in particular, tetra-n-butylammonium bromide. The catalyst may be added in a quantity between 0.02 up to 0.5 equivalent and preferably 0.05 up to 0.15 equivalents with respect to each carbamate functional group to be reacted.

According to a second embodiment of the invention, the reaction is carried out in the presence of an agent capable of neutralizing the halohydric acid, which is produced during the reaction. Particularly suitable for this purpose within the scope of the present invention are the substances, which are acid acceptors and which do not exhibit a substantial nucleophilic activity, but which are sufficiently strong bases in order to form a complex with the acid formed. The preferred substances are selected from the group, which comprises pyridines substituted in the 2,4- or in the 2,4,6-position by aliphatic radicals, which may have one carbon atom, for instance, a methyl group and up to n carbon atoms, the symbol n being sufficiently high so that the radical may be a polymeric chain; anilines substituted on the N atom by alkyls having between 1 and n carbon atoms, n being sufficiently high so that the radical may be a polymeric chain and in particular, substituted anilines in which the aromatic ring is deactivated by electrophilic substituents, for instance, halogen atoms, particularly in the para position; certain alkenes, such as pinene or cyclododecatriene, aromatic diisocyanates such as toluene diisocyanate or aliphatic diisocyanates such as those of the formula $O=C=N(CH_2)_xN=C=O$ in which x is an integer number between 6 and 36; and alkali or alkaline earth carbonates. Particularly suitable are collidine, p-halo-N,N-dialkylanilines and pinene.

The acid acceptor is used in a quantity equal to or greater than the stoichiometric amount and preferably in slight to substantial excess.

In addition to chemical methods, it is possible to remove by physical methods, the halohydric acid, which if left in the reaction medium, could slow down the reaction and also destroy the product. For instance, the reaction may be performed at reduced pressure to suck out the acid as soon as formed. This may be achieved by using a system with a high surface area such as a thin film evaporator to facilitate the escape of the acid. It is also possible to pass an inert gas for instance, nitrogen or argon, through or over the reaction medium to entrap the acid in the gas and thus remove it as soon as formed, at lower pressure or atmospheric pressure or even at high pressure.

It is also possible to use molecular sieves for instance, 3 Å for hydrogen chloride.

According to another embodiment of the invention, the dehydrohalogenation may be carried out in the presence of at least one aprotic solvent, which is weakly nucleophilic or not nucleophilic and optionally also a polar solvent The solvent may be selected from the group which comprises ethers such as triglyme, (triethylene glycol dimethyl ether), sulfones, N,N-dialkylsulfonamides, N,N,N',N'-tetralkylsulfonylureas, aromatic hydrocarbons and preferably aromatic hydrocarbons which have a suitable boiling point and at least one electron withdrawing (electrophilic) substituent, alkanes or alkenes which have a suitable boiling point such as dichloroethane and tri- or tetrachloroethylene and even the final product, that is the dehydrohalogenated carbamates. Chlorobenzene, bromobenzene, dichlorobenzenes, trichlorobenzenes, tetrachlorobenzenes, and tetrachloroethylenes are among the most suitable solvents. The use of solvents simplifies frequently the recovery of the products. Preferably, one selects the conditions of temperature and pressure in a manner to lead the solvent to reflux.

A period of time of a few hours is usually sufficient to obtain the vinyl carbamates. It is preferable to carry out the reaction in an anhydrous medium in the absence of oxygen for instance, in a nitrogen atmosphere. The vinyl carbamates are recovered by conventional methods, for instance after appropriate elimination of the solvent or if more volatile may be recovered by distillation from the solvent.

According to a preferred embodiment of the process, the reaction is carried out in the presence of a catalyst as described above, in the presence of an organic acceptor of the acid as described above, and in the presence of a solvent as described above. Excellent yields often are obtained by the use of tetra-n-butyl-ammonium bromide and collidine in the presence of a solvent such as chlorobenzene or tetrachloroethylene.

An essential feature of the process according to the present invention resides in the fact that the α-halogenated carbamates of formula II are heated to a temperature between 70° and 250° C. in order to achieve dehydrohalogenation. One preferably operates at a temperature between 80° and 200° C.

It is possible and sometimes convenient to form the α-halogenocarbamate and eliminate H-X to give the desired product vinyl carbamate in one step without isolating the intermediate α-halogenocarbamate. For example, when heat is used in the synthesis of the α-halogenocarbamate, the reaction may often be performed so that the elimination occurs almost as soon as the halogenocarbamate is generated. Indeed, some of the halogenocarbamate may be undergoing elimination before the remainder has been completely formed. If the elimination is not complete under these conditions, the remaining halogenocarbamate can be converted to the derived vinyl carbamate by subjecting the mixture of the two substances to any of the conditions described herein to convert essentially pure α-halogenocarbamates of similar structure to their vinyl carbamates.

The invention is illustrated by the examples hereinbelow.

In the examples below, ACE is often used as an abbreviation for the CH₃—CHCl—O—C(=O)—group and VOC is often used as an abbreviation for the CH₂=CH—O—C(=O)—group. Thus, ACE-Cl means α-chloroethyl chloroformate.

EXAMPLE 1

Preparation of N-Isobutenyloxycarbonyl-N-methylcyclohexylamine

(a) Synthesis of N-α-Chloroisobutyloxycarbonyl-N-methylcyclohexylamine

A solution of N-methylcyclohexylamine (Aldrich, dried over KOH and distilled) (14.9 g, 0.13 mol) in 15 cc of ether was added slowly (15 minutes) to a stirred solution of α-chloroisobutyl chloroformate (9.91 g, 0.058 mol) in 15 cc ether cooled to 0° C. After the addition was complete, the mixture was warmed to room temperature and stirred for another hour. The salts were filtered off and the filtrate was rotoevaporated before isolation of the product by simple vacuum distillation; 13.3 g (92% yield) of boiling point 111°–113° C. at 0.6 mm.

IR (μ): 3.49 (m), 5.81 (vs); CCl₄.

¹H NMR(δ): 6.30 (d,J=4), 4.2–3.4 (m), 2.80 (s), 2.4–0.8 (m with methyl d at 1.05, J=6); ratio 1:1:3:17; CCl₄.

MS (m/e): 249.1319 (P[³⁷Cl], 6%, Calc. 249.1310), 247.1344 (P[³⁵Cl], 21%, Calc. 247.1339), 206.0760 (P[³⁷Cl]—CH(CH₃)₂, 8%, Calc. 206.0762), 204.0789 (P[³⁵Cl]—CH(CH₃)₂, 26%, Calc. 204.0791), 157 (17%), 156 (88%), 140 (69%), 114 (68%), 58 (100%).

(b) Dehydrohalogenation

The chlorocarbamate (4.58 g, 0.0185 mol) was heated in an oil bath at 170° C. in a 25 cc round bottomed flask equipped with a reflux condenser and nitrogen inlet. Vigorous evolution of HCl gas occurred during the first 30 minutes of reaction and after 1 hour the process was 94% complete as determined by NMR analysis. After 2 hours, the product alkenyl carbamate was distilled directly from the reaction mixture giving 3.29 g (84% yield, NMR pure) of boiling point 98°–102° C. at 0.4 mm. An additional 0.46 g of residue remained in the distillation pot and this analyzed (NMR) as about a 1:1 mixture of N-methylcyclohexylamine hydrochloride and the product.

IR(μ): 3.49 (m), 5.84 (vs); CCl₄.

¹H NMR(δ): 7.0–6.7 (m), 4.3–3.5 (m), 2.83 (s), 2.2–0.5 (m); ratio 1:1:3:16; CCl₄.

MS (m/e): 211.1573 (P, 7%, Calc. 211.1573), 140.1066 (P—OCH=C(CH₃)₂, 45%, Calc. 140.1075), 83 (100%), 72 (42%).

(c) N-α-Isobutenyloxycarbonyl-N-methylcyclohexylamine

A solution of N-α-chloroisobutyloxycarbonyl-N-:methylcyclohexylamine, (10.1 g, 0.041 mole), 2,4,6-collidine (6.0 g, 0.050 mol), tetrabutyl ammonium bromide (0.75 g, 0.002 mol), and tetrachloroethylene (19 cc) was heated at 125° C. for 2 hours. After a standard extraction workup (ether and 1N H₂SO₄) and rotoevaporation, the product alkenyl carbamate was isolated pure (NMR) by vacuum distillation; 8.50 g (99% yield) of boiling point 93°–98° C. at 0.2 mm.

EXAMPLE 2

Preparation of N-Vinyloxycarbonylpiperidine (VOC-piperidine)

(a) Preparation of N-α-Chloroethoxycarbonylpiperidine (ACE-piperidine)

A solution of N-ethylpiperidine (Aldrich, distilled) (5.68 g, 0.05 mol) in 20 cc of dichloroethane was dripped. (15 minutes) into a stirred and ice-cooled solution of ACE-Cl (9.32 g, 0.065 mol), 1,8-bis-(dimethylamino)naphthalene, (0.53 g, 0.0025 mol, 0.05 equiv.), and 50 cc of dichloroethane. During the addition the solution color turned from clear to yellow and remained this color while the reaction was cold. The mixture was refluxed for 30 minutes, cooled and the solvent and excess ACE-Cl removed in vacuo. Then the remaining dark red liquid was distilled at 0.2 mm to afford 9.36 g (97% yield) of colorless title carbamate; boiling point 67°–69° C. at 0.2 mm.

IR (μ): 3.40 (m), 3.50 (m), 5.80 (vs), 7.01 (s); CCl₄.

¹H NMR (δ): 6.48 (q, J=6), 3.8–3.0 (m), 1.9–1.2 (m with methyl d at 1.75); ratio. 1:4:9; CCl₄.

MS (m/e): 193:0653 (P[³⁷Cl], 4%, Calc. 193,0684), 191.0700 (P[³⁵Cl], 11%, Calc. 191.0700), 128.0712 (P[³⁵Cl]—CHClCH₃, 100%, Calc. 128.0712), 112.0758 (P[³⁵Cl]—OCHClCH₃, 59%, Calc. 112.0762), 84.0808 (73%).

(b) Dehydrochlorination

In a glass reactor equipped with a magnetic stirrer, a thermometer, and a reflux condenser connected with a vacuum system, there was introduced 9.8 grams of N-α-chloroethoxycarbonyl-piperidine of formula:

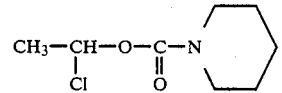

and 4.8 grams (0.30 equivalent), of anhydrous tetra-n-butylammonium bromide. The mixture was refluxed at a pressure of 0.3 mm of mercury for a period of six days, (oil bath at 105° C.). The reaction product was then distilled off under reduced pressure: VOC-piperidine was obtained. Boiling Point 60°–61° C. at 0.3 mm mercury. Yield: 78%. On infrared analysis, the substance gave the following bands (μ): 5.81; 6.07; 8.57; in CCl₄.

EXAMPLE 3

Preparation of N-Vinyloxycarbonylpiperidine

This experiment was carried out in the same manner as Example 2 from the same reactants, but the mixture was refluxed at 0.3 mm (oil bath between 85° and 95° C.) for a period of 18 hours. Then methanol was added and the mixture was refluxed for one hour and the methanol removed at reduced pressure. The remaining oil was partitioned between ether and water. The ether layer was evaporated to give pure VOC-piperidine in 54% yield.

EXAMPLE 4

Preparation of N-Vinyloxycarbonyl-piperidine

In a glass reactor kept under vacuum, 0.55 grams of calcium chloride was dried for a period of onehalf hour. There was then introduced N-α-chloroethoxycarbonyl-piperidine in the amount of 0.75 cc. The temperature of the oil bath was kept at 130° C. and the vacuum was 40 mm of mercury. After one hour and 15 minutes, the ratio of product to starting material measured by NMR was 0.2:1. After 20 hours, the ratio vinyl carbamate to α-chloroethyl carbamate was 4.6 determined by NMR.

EXAMPLE 5

Preparation of N-Vinyloxycarbonylpiperidine

This experiment was carried out in the same manner as the preceeding experiment, but calcium chloride was replaced by lithium bromide. The mixture was heated for 1½ hours. The ratio of vinyl carbamate to α-chloroethyl carbamate determined by NMR was 1:1.

EXAMPLES 6–10

Preparation of N-Vinyloxycarbonylpiperidine

These experiments illustrate the dehydrochlorination in the presence of different catalysts and different solvents.

In these examples, the manner of operation was as follows:

In a reactor provided with reflux condenser and a nitrogen inlet, there were introduced the organic solvent, the N-α-chloroethoxycarbonylpiperidine and the catalyst. The mixture was heated under reduced pressure under conditions to permit the solvent to reflux mildly at the temperature of operation. The experimental conditions, the materials used and the results are summarized in Table 1. The yields given were determined by NMR spectroscopy on the reaction mixture at the end of the listed reaction time.

point 172° C.), and o-dichlorobenzene (20 cc, 0.18 mol, boiling point 178° C.) was heated to 185° C. in an oil bath, allowed to reflux for 3 hours and then cooled to room temperature. The mixture had darkened considerably and some collidine hydrochloride had precipitated. Chloroform was added until the mixture was homogeneous. This solution was washed with water (3×50 cc) which removed almost all of the color and the aqueous layers were combined and extracted with chloroform (2×30 cc). The chloroform extracts were combined, dried (Na$_2$SO$_4$) and roto-evaporated. The product, VOC-piperidine, was isolated by means of an efficient vacuum distillation through a 35 cm vacuum-jacketed column with a Teflon inner coil. The column was wrapped with heating tape kept 15°–20° C. lower than the distillation temperature. The o-dichlorobenzene fraction was followed by an intermediate fraction of boiling point 95°–123° C. at 47 mm (2.07 g) which contained (NMR analysis) o-dichlorobenzene, collidine (3 mol %), and VOC-piperidine(31 mol %, 9% absolute yield). The final distillation fraction, 6.21 g of boiling point 123°–128° C. at 47 mm, analyzed (NMR) as pure VOC-piperidine (80% yield; total product in both fractions 89%). Almost no residue remained in the still pot.

EXAMPLE 12

Preparation of VOC-Piperidine

In a similar experiment, bromobenzene (20 cc, 0.19 mol, boiling point 156° C.) was used as the inert solvent-diluent. The solution containing the bromobenzene, ACE-piperidine (10.0 g, 0.052 mol), and collidine (7.70 g, 0.064 mol) was heated to 170° C. in an oil bath and the mixture was allowed to reflux for 5.5 hours prior to cooling at room temperature. The reaction mixture was partitioned between water (20 cc) and ether (40 cc). The layers were separated, the organic layer was washed with water (2×20 cc), and the combined aqueous extracts were washed with ether (2×25 cc). The organic layers were combined, dried (Na$_2$SO$_4$), roto-

TABLE I

| Ex. | N—α-chloroethoxy-carbonyl-piperidine quantity in g. | Catalyst | Quantity in g | in eq. | Solvent | Temp. °C. | Reaction Time | Yield VOC-Piperidine % |
|---|---|---|---|---|---|---|---|---|
| 6 | 0.92 | tetra-N—butyl-ammonium bromide | 0.16 | 0.10 | bromo-benzene 2 cc | 130 | 24 hours | 78 |
| 7 | 0.92 | KCl + 18-crown-6 | 0.18 0.13 | 0.5 0.10 | bromo-benzene 2 cc | 130 | 24 hours | 53 |
| 8 | 0.97 | tetra-N—butyl-ammonium bromide | 0.09 | 0.055 | o-dichloro-benzene 2 cc | 150 | 20.5 hrs. | 80 |
| 9 | 0.92 | tetra-N—butyl-ammonium bromide | 0.092 | 0.059 | triglyme 2 cc | 170 | 20 mins. | 55 |
| 10 | 7.190 | KCl + 18-crown-6 | 0.96 0.47 | 0.35 0.05 | 1,2,4,6-tetra-chloroben-zene (28 g) | 190 | 4.5 hrs. | 61 |

EXAMPLE 11

Preparation of N-Vinyloxycarbonylpiperidine (VOC-Piperidine) from ACE-Piperidine in the Presence of Collidine A stirred solution (under N$_2$) of ACE-Piperidine (9.6 g, 0.05 mol), 2,4,6-collidine (7.4 g, 0.06 mol, boiling evaporated, and distilled using the apparatus described in Example 11. The bromobenzene fraction was followed by a small intermediate fraction, 0.43 g of boiling point 100°–124° C. at 44 mm, which analyzed (NMR) as a mixture of collidine (56 mol %), bromobenzene (27 mol %), and VOC-piperidine (17 mol %). The main product fraction, 7.31 g of boiling point 124°–126° C. at 44 mm, analyzed as VOC-piperidine contaminated by 3.5 mol % of 2,4,6-collidine (yield of VOC-piperidine 88%). The collidine contaminant could be removed by extraction with dilute aqueous sulfuric acid.

EXAMPLE 13

Preparation of VOC-Piperidine

Another experiment was performed on an NMR scale in which collidine was used both as the solvent and the acid sequestering agent. In this experiment, ACE-piperidine (1.12 g) in 3 cc of collidine (3.9 equiv.) was heated for 1 hour at 170° C. Based on NMR analysis, a 52% yield of VOC-piperidine was present in the reaction medium and 33% of the starting ACE-piperidine remained. Decomposition products accounted for the remainder of the starting material.

EXAMPLE 14

Preparation of VOC-Piperidine

VOC-Piperidine from ACE-Piperidine using Collidine and using additional VOC-Piperidine as the solvent diluent A stirred solution (under $N_2$) of ACE-piperidine (8.33 grams, 0.043 mol), 2,4,6-collidine (6.43 grams, 0.053 mol), and VOC-piperidine (15.6 grams, 0.1 mol) was heated at 185° C. for 3 hours in an oil bath, then cooled, and partitioned between ether (25 ml) and 1N $H_2SO_4$ (20 ml). The layers were separated and the organic layer was washed with additional 1N $H_2SO_4$ (2×20 cc) and brine (20 cc). The combined aqueous acid layers were back extracted with ether (2×20 cc) which was then used to back extract the brine solution. The ether extracts were combined, dried ($Na_2SO_4$), the ether evaporated at reduced pressure, and the VOC-piperidine isolated by simple vacuum distillation; 20.6 g of material, b.p. 60°–61° C. at 0.3 mm (yield after subtraction of 15.6 grams included at beginning: 75%) was obtained. The product was pure (NMR analysis). Some residue remained in the still pot.

EXAMPLE 15

Preparation of VOC-Piperidine

Into a glass reactor was introduced 0.932 grams of ACE-piperidine, 0.098 grams (0.063 equiv.) of tetra-n-butylammonium bromide and 2 cc, (2.6 equiv.) of N,N'-diethylaniline. The mixture was heated at 150° C. for 30 minutes. The analysis (NMR) showed that the product was VOC-piperidine in 59% yield and that 10% decomposition had occurred. The ratio of VOC-piperidine to ACE-piperidine was 1.9:1 (NMR).

EXAMPLE 16

Preparation of VOC-Piperidine from ACE-Piperidine in the Presence of Collidine and Tetrabutylammonium bromide A stirred solution (under $N_2$) of ACE-piperidine (11.5 grams, 0.06 mol), tetrabutylammonium bromide (0.97 grams, 0.003 mol), and 2,4,6-collidine (8.72 grams, 0.07 mol) in chlorobenzene (25 cc, 0.25 mol), boiling point 132° C.) was heated to 140° C. in an oil bath, allowed to reflux for 21 hours, and then cooled to room temperature. Ether (40 cc) was added to the mixture which then was extracted with 1N $H_2SO_4$ (3×30 cc) and brine (30 cc). The aqueous layers were combined and back extracted with ether (2×40 cc). The combined ether extracts were dried ($Na_2SO_4$), rotary evaporated, and the chlorobenzene distilled off (boiling point 55°–57° C. at 55 mm). The VOC-piperidine was isolated by reduced pressure distillation; boiling point 130°–132° C. at 55 mm; 8.2 grams (88% yield); NMR pure.

In another experiment under the same conditions except that the reaction mixture was refluxed for 28 hours, the yield of distilled VOC-piperidine was 89%.

In spite of the fact that the catalyst decomposed under the reaction conditions, it still significantly increases the reaction rate as demonstrated by the following experiment. ACE-Piperidine (10.4 grams, 0.054 mol), 2,4,6-collidine (8.00 grams, 0.066 mol), and chlorobenzene (25 cc) were heated at 140° C. for 27 hours. Analysis by NMR indicated that the reaction was only 84% complete. Therefore, the reaction was continued at 140° C. for a total reaction time of 48 hours. Workup as described above afforded VOC-piperidine in 70% yield.

Other salts also increase the reaction rate. In another experiment, a mixture of ACE-piperidine (1.78 grams, 9.3 mmol), 2,4,6-collidine (1.38 grams, 11.4 mmol), ammonium chloride (0.10 grams, 1.9 mmol), and chlorobenzene (4 cc, 39.3 mmol was heated at 140° C. for 25 hours and then cooled to room temperature. Ether (20 cc) was added and the mixture was extracted with 1N $H_2SO_4$ (2×20 cc). The combined aqueous layers were backwashed with ether (20 cc). The organic layers were combined, dried ($Na_2SO_4$), and rotary evaporated. 1,1,2,2-tetrachloroethane (1.57 grams, 9.35 mol) was added to the remaining oil as a quantitative internal standard for NMR analysis; calculated yield 63%

EXAMPLE 17

Preparation of N,N'-Di(vinyloxycarbonyl)piperazine (Di-VOC-piperazine)

(a) N,N'-Di(α-chloroethoxycarbonyl)-piperazine; (Di-ACE-oioerazine)

A solution of N,N'-dimethylpiperazine (Aldrich, dried over KOH and fractionally distilled) (9.50 g, 0.083 mol) in 1,2-dichloroethane (40 ml) was dripped (35 min) into a stirred solution of α-chloroethyl chloroformate (32.5 g, 0.227 mol) and 1,8-bis(dimethylamino)naphthalene (1.94 g, 0.009 mol, 0.11 equiv.) in dichloroethane (100 cc) kept at −5° C. During the addition of the piperazine, a white solid precipitated which decreased the efficiency of mixing, but when the reaction temperature was raised to reflux, the solid dissolved. After refluxing for 1 hour, the reddish-brown solution was cooled, charcoal was added, dry HCl was bubbled slowly through the solution for 30 seconds to complex the excess bis(dimethylamino)naphthalene, and the solution was passed through a ¾"×2" plug of Silica Gel with methylene chloride as the eluant. Vacuum evaporation of the resulting clear solution afforded an off-white solution which was dried overnight in vacuo at 55° C.; yield 97% (24.0 g, NMR pure) of the title dicarbamate with a m.p. of 125.5°–135.5° C. (most of the solid melted at 125.5°–130° C.). The solid had a m.p. of 131.5°–138° C. after recrystallization from 1,2-dichloroethane, but its spectral and TLC purity was unchanged. Since the solid product is probably a mixture of a pair of diastereomers, the melting point is not a good indication of purity, but only an indication of variation in diastereomer ratio. The two chiral centers, however, are too far apart to show the presence of diastereomers in the NMR spectrum.

IR (μ): 5.79 (vs), 8.17 (m), 9.17 (s); CHCl₂.

¹H NMR (δ): 6.58 (q, J=6), 3.52 (broad d), 1.79 (d, J=6); ratio 2:8:6; CDCl₃.

MS (m/e): 300.0447 (P[$^{37}$Cl, $^{35}$Cl], 2%, Calc. 300.0457), 298.0471, (P[$^{35}$Cl₂], 4%, Calc. 298.0487), 237 (7%), 235.0476 (P[$^{35}$Cl]—CHClCH₃, 19%, Calc. 235.0485), 221 (7%), 219.0530 (P[$^{35}$Cl—]—OCHClCH₃, 12%, Calc. 219.0536), 191 (28%), 177 (34%), 175 (100%), 155 (43%), 149 (66%), 113 (32%).

(b) Conversion of N,N'-Di-ACE-piperazine to N,N'-Di-VOC-piperazine.

A solution of N,N'-di-ACE-piperazine (7.61 g, 0.025 mol), 2,4,6-collidine (6.96 g, 0.057 mol), and o-dichlorobenzene (20 cc) was heated (oil bath at 185° C.) for 45 minutes. Chloroform (40 cc) was added to the cooled, dark-red solution which then was extracted with 1 N H₂SO₄ (3×30 cc) and brine (20 cc). The aqueous extracts were back-extracted with chloroform (2×25 cc). The combined organic layers were dried (Na₂SO₄), charcoal was added, and the solvent was removed in vacuo. The solid residue was passed through a silica gel plug (CH₂Cl₂ as eluant). The eluate was evaporated at reduced pressure yielding N,N'-di-VOC-piperazine as a light tan solid; 1.88 g (33% yield, NMR pure). The rechromatographed sample used for analysis had a melting point of 97.5°–99° C.

IR (μ): 5.86 (vs), 6.06 (m); CH₂Cl₂.

¹H NMR (δ): 7.21 (d of d, J=14, 6), 4.80 (d of d, J=14, 1), 4.48 (d of d, J=6, 1), 3.54 (s); ratio 2:2:2:8; CDCl₃.

MS (m/e): 226.0947 (P, 15%, Calc. 226.0953), 183.0762 (P—OCH=CH₂, 98%, Calc. 183.0770), 139 (42%), 113 (100%), 97 (28%).

In a related experiment performed in bromobenzene (6.6 equiv) at reflux in the presence of 2.3 equiv. 2,4,6-collidine, the reaction was 42% complete (NMR analysis) after 2 hours.

In another experiment, a solution of N,N'-di-ACF-piperazine (5.15 g, 0.017 mol , tetra-n-butylammonium bromide (0.51 g, 0.002 mol), 2,4,6-collidine (4.91 g, 0.041 mol), and tetrachloroethylene (18 cc) was heated at reflux. After 3 hours, NMR analysis indicated that the reaction was 28% complete. The reaction mixture was worked up as above after 24 hours and the N,N'-di-VOC-piperazine was isolated.

Reaction of N,N'-di-ACE-piperazine (1.71 g, 5.72 mmol) in dichloroethane (20 cc) in the presence of benzyltri-n-butylammonium chloride (1.30 g, 4.15 mmol) was performed at reflux overnight with N₂ bubbling through the solution and allowing the solvent to evaporate. The remaining brown oil solidified upon cooling. This was partitioned between CH₂Cl₂ (50 cc) and 0.01 N HCl (40 cc). The organic layer was dried (Na₂SO₄), evaporated, and then heated in 5 cc of methanol at 65° C. After evaporation and attempted sublimation, the product was chromatographed through silica. The yield of chromatographed N,N'-di-VOC-piperazine was 33%.

N,N'-Di-VOC-piperazine also was produced in the absence of catalyst, solvent, or base. When N,N'-di-ACE-piperazine (0.62 g, 2.07 mmol) was heated at 185° C. in a 100 mm vacurm, to remove HCl as formed, for 1 hour, NMR analysis indicated 34% conversion to VOC and 10% decomposition of the starting material.

In a final experiment (−)-β-pinene was used to scavenge the HCl. N,N'-Di-ACE-piperazine (10.1 g, 0.034 mol), (−)-β-pinene (11.1 g, 0.082 mol), and o-dichlorobenzene (25 cc) were refluxed (oil bath at 185° C.). After 20 hours, NMR analysis showed the reaction was 70% complete. After hours, the solvent was removed at reduced pressure, charcoal was added, and the product was passed through a silica gel plug (CH₂Cl₂ as eluant). NMR analysis of the chromatograhed product (4.29 g) gave a VOC to ACE ratio of 86:14; absolute yield of di-OC-piperidine: 40%.

EXAMPLE 18

Preparation of N-Vinyloxycarbonyl-N-methylaniline (N-VOC-N-methylaniline)

(a) Preparation of N-ACE-N-Methylaniline.

N,N-Dimethylaniline (19.3 grams, 0.16 mol) in dichloroethane (25 cc) was slowly added to a stirred, cooled (0° C.) solution of ACE-Cl (49.8 grams, 0.35 mol) in dichloroethane (75 cc). This mixture was heated to 90° C. (oil bath) and refluxed for 3 days. The solvent and excess ACE-Cl were removed by vacuum evaporation. A black oil was obtained to which ether, (which precipitated out a black solid) and charcoal were added. The solids were filtered off, the solvent removed, and the product isolated by vacuum distillation; 29.3 grams (86% yield, NMR pure) of boiling point 100°–110° C. at 0.4 mm.

IR (μ): 5.78 (vs), 6.25 (m), 6.67 (m); CCl₄.

¹H NMR (δ): 7.6–6.9 (m), 6.55 (q,J=6), 3.21 (s), 1.60 (d, J=6); ratio 5:1:3:3; CCl₄.

MS (m/e): 215.0562 (P[$^{37}$Cl], 38%, Calc. 215.0527), 213.0573 (P[$^{35}$Cl], 71%, Calc. 213.0556), 151.0646 (P—C₂H₃Cl, 64%, Calc. 151.0634), 134.0594 (P—OCHClCH₃, 100%, Calc. 134.0606), 107 (64%), 106 (76%), 77 (69%), 63 (80%).

(b) Collidine Facilitated Conversion of N-ACE-N-Methylaniline to N-VOC-N-Methylaniline.

A stirred mixture (under N₂) of N-ACE-N-methylaniline (10.4 grams, 0.048 mol), 2,4,6-collidine (7.15 grams, 0.059 mol, and o-dichlorobenzene (20 cc, 0.18 mol) was heated at 185° C. for 3 hours in an oil bath and then cooled to room temperature. The mixture was partitioned between water and ether, the layers separated, the organic layer washed with water, dried (Na₂SO₄), and evaporated at reduced pressure. The N-VOC-N-methylaniline product was isolated by vacurm distillation through a short Vigreaux column; 2.72 grams (32% yield, NMR pure) of boiling point 75°–79° C. at 0.4 mm.

IR (μ): 5.78 (vs), 6.06 (m), 6.25 (m), 6.67 (m); CCl₄.

¹H NMR (δ): 7.5–6.8 (m), 4.57 (d of d, J=14, 1), 4.30 (d of d, J=7, 1), 3.20 (s); ratio 6:1:1:3; CCl₄.

MS (m/e): 177.0793 (P, 58%, Calc. 177.0790), 134.0608 (P—OCH=CH₂, 100%, Calc. 134.0606),119.0371 (P—C₃H₆O, 12%, Calc. 119.0371), 106.0655 (P—CO₂CH=CH₂, 81%, Calc. 106.0657), 77.0391 (C₆H₅, 81%, Calc. 77.0391),51 (28%).

EXAMPLE 19

Preparation of N-Vinyloxycarbonylmorpholine (a) Preparation of N-α-chloroethoxycarbonylmorpholine (ACE-Morpholine) A sample of N-methylmorpholine was converted to N-α-chloroethoxycarbonylmorpholine in 96% yield by reaction in the same manner as in Example 18; boiling point 84°–86° C. 00.4 mm. at IR (μ): 5.79 (vs), 7.82 (m), 8.08 (s), 9.11 (s); CCl₄.

¹H NMR (δ): 6.50 (q, J=6), 3.8–3.2 (m), 1.76 (d, J=6); ratio 1:8:3; CCl₄.

MS (m/e): 195.0462 (P[$^{37}$Cl], 3%, Calc. 195.0476), 193.0494 (P[$^{35}$Cl], 8%, Calc. 193.0506), 180.0237 (P[$^{37}$Cl]—CH₃, 6%, Calc. 180.0241), 178.0269 (P[$^{35}$Cl]—CH₃, 19%, Calc. 178.0271), 130.0500

(P—CHClCH$_3$, 39%, Calc. 130.0504), 114.0550 (P—OCHClCH$_3$, 71%, Calc. 114.0555), 70 (67%), 69 (38%), 63 (100%).

(b) Conversion of ACE-Morpholine to VOC-Morpholine.

A stirred mixture of ACE-morpholine (11.3 grams, 0.058 mol) and 2,4,6-collidine (8.79 grams, 0.073 mol) in o-dichlorobenzene (25 cc, 0.22 mol) was heated at 185° C. for 2 hours in an oil bath, (NMR analysis at the 1.5 hour mark showed the reaction to be 96% complete). After the normal ether/1N H$_2$SO$_4$ extraction workup and rotoevaporation, the product was isolated by vacuum distillation through a 35 cm vacuum jacketed column with a Teflon inner coil. The solvent was removed (boiling point 93°-94° C. at 49 mm) followed by a fraction which contained 9 mol % VOC-morpholine (1.90 grams, boiling point 109°-126° C. at 49 mm, calculated yield 2%). The product then distilled over; 7.32 grams (80% yield, NMR pure) of boiling point 134°-136° C. at 49 mm (overall yield 82).

IR($\mu$) 5.81 (vs), 6.07 (m); CCl$_4$.

$^1$H NMR($\delta$): 7.20 (d of d, J=14, 7), 4.68 (d of d, J=14, 1) and 4.40 (d of d, J=7, 1), 3.9–3.2 (broad); ratio 1:2:8; CCl$_4$.

MS (m/e): 157.0732 (P, 14%, Calc. 157.0739), 114.0563 (P—OCH=CH$_2$, 88%, Calc. 114.0555), 70 (100%).

EXAMPLE 20

Preparation of 1-(Isobutenyloxycarbonyl)benzotriazole.

(a) 1-($\alpha$-Chloroisobutyloxycarbonyl)benzotriazole.

$\alpha$-Chloroisobutyl chloroformate (7.85 grams, 0.046 mol) in ether (10 cc) was added (10 min) to a stirred, cooled (0° C.) solution of benzotriazole (Aldrich) (11.6 grams, 0.097 mol), ether (50 cc), and methylene chloride (10 cc). After the addition was complete (10 min), the mixture wa.s stirred at room temperature for 1 hour. Excess benzotriazole was removed by bubbling HCl into the mixture and then removing all salts by filtration. The product then was passed through a silica gel plug (CH$_2$Cl$_2$ as eluant). The clear oil obtained after rotary evaporation of the solvent (11.5 grams, 99% yield) later solidified (melting point 42°-b 52° C.).

IR ($\mu$) 5.65 (vs), 6.19 (w), 6.23 (w), 6.71 (m), 6.86 (vs), 7.10 (vs); CCl$_4$.

$^1$H NMR ($\delta$): 8.3–7.3 (m), 6.63 (d, J=5), 2.9–2.2 (m), 1.22 (d, J=6); ratio 4:1:1:6; CDCl$_3$.

MS (m/e): 255.0582 (P[$^{37}$Cl], 6%, Calc. 255.0588), 253.0626 (P[$^{35}$Cl , 18%, Calc. 253.0618), 146 (85%), 135 (20%), 119 (37%), 118 (43%), 91 (67%), 90 (92%), 55 (100%).

(b) Conversion of 1-($\alpha$-Chlqroisobutyloxycarbonyl)-benzotriazole to 1-(Isobutenyloxycarbonyl)benzotriazole.

The chloroisobutyloxycarbonylbenzotriazole (4.72 grams, 0.019 mol) and tetrabutylammonium bromide (0.29 grams, 0.001 mol), were dried overnight in vacuo at 50° C. Tetrachloroethylene (10 cc) and 2,4,6-collidine (2.83 grams, 0.023 mol) were added and the mixture was refluxed (125° C. oil bath) for 9 hours (by NMR analysis the reaction was 70% complete after 3 hours). The dark red solution was passed through a silica gel plug (CH$_2$Cl$_2$ as eluant). The red oil remaining after rotary evaporation was passed through another silica plug eluted with ether: hexane (1:1). Rotary evaporation afforded the product as a yellow oil (2.48 grams, 61% crude yield). Crystallization from hexane produced a yellow solid (1.81 grams, more than 95% pure by NMR analysis, 43% yield). The filtrate also contained about 50% product (NMR analysis) (total yield 50%). The product was recrystallized again from hexane, melting point 47°-49° C., Martz (Ph.D. Thesis, The Pennsylvania State University, 1982) reported a melting point of 47°-49.5° C. for the product obtained by treating benzotriazole-1-carbonyl fluoride with isobutenyloxytrimethylsilane. The spectral properties listed below matched those given by Martz, (loc. cit.).

IR($\mu$): 5.68 (vs), 6.21 (w), 6.24 (w), 6.72 (s), 6.89 (s), 7.15 (vs); CH$_2$Cl$_2$.

$^1$H NMR ($\delta$): 8.3–7.2 (m), 7.2–6.9 (m), 1.90 (s), 1.76 (s); ratio 4:1:3:3; CDCl$_3$.

When the reaction was performed in o-dichlorobenzene at 170° C. for 1 hour (no (nBu)$_4$N$^+$ Br$^-$ present), the product yield (NMR analysis) was 30% and much starting material and decomposition products also were present. When chloroisobutyloxycarbonylbenzotriazole was heated at 170° C. under vacuum (160 mm) for 2 hours, the product was formed in 10% yield (NMR analysis) and the remainder of the mixture consisted almost exclusively of starting material.

EXAMPLE 21

Preparation of N(E,Z-Propenyloxycarbonylmorpholine (a) N-($\alpha$-Chloropropyloxycarbonyl)morpholine.

A solution of morpholine (Aldrich, dried over KOH and distilled) (16.1 grams, 0.18 mol) in ether (25 cc) was added (15 minutes) to a stirred, cooled (0° C.) solution of 1-chloropropyl chloroformate (13.0 grams,$^-$ 0.083 mol) in ether (25 cc). The mixture was stirred for 1 hour at room temperature, the salts filtered off, the filtrate concentrated, and the product distilled; boiling point 95°-97° C. at 0.9 mm, 14.4 grams (84% yield).

IR($\mu$): 5.81 (vs); CCl$_4$.

$^1$H NMR ($\delta$): 6.37 (t, J=6), 3.9–3.2 (broad), 2.02 (pentet, J=6,7), 1.02 (t, J=7); ratio 1:8:2:3; CDCl$_3$.

MS (m/e): 209.0636 (P[$^{37}$Cl], 6%, Calc. 209.0633), 207.0662 (P[$^{35}$Cl], 20%, Calc. 207.0662), 130.0503 (P-CHClEt, 27%, Calc. 130.0504), 114.0562 (P-OCHClEt, 81%, Calc. 114.0555), 41 (100%).

(b) Conversion of N-(1-Chloropropyloxycarbonyl)morpholine to N-(E,Z-Propenyloxycarbonyl)morpholine.

A stirred mixture of 1-chloropropyloxycarbonylmorpholine (11.9 grams, 0.057 mol), 2,4,6-collidine (8.6 grams, 0.071 mol), n-tetrabutylammonium bromide, (0.94 grams, 0.003 mol), and tetrachloroethylene (25 cc) was heated at 125° C. in an oil bath for 24 hours (by NMR analysis, the reaction was ca. 70% complete after 5 hours). After the standard extraction workup, ether and other volatiles were distilled off and the product was isolated by vacuum distillation, boiling point 86°-90° C. at 0.5 mm, 8.2 grams (84% yield). The spectral properties given below match those reported by Olofson and Cuomo, Tetrahedron Lett., 21, 819, (1980). Based on the spectral analyses and Olofson and Cuomo's data for the pure isomers, the E:Z ratio for the new product is 1:1.8.

IR ($\mu$): 5.81 (vs), 5.95 (w); CCl$_4$. $^1$H NMR ($\delta$): 7.2–6.8 (m), 5.19 (d of q, J=1.5,7, E-isomer), 4.73 (d of q, J=7,7, Z-isomer), 3.9–3.2 (broad), 1.8–1.5 (m); ratio 1:0.36:0.64:8:3; CCl$_4$.

When the dehydrochlorination was performed in bromobenzene, (oil bath at 170° C., without the tetrabutylammonium bromide) for 90 minutes, the estimated yield of product (NMR) was 55% (E:Z 1:2.0): about 25% of the starting material remained, and the remainder was accounted for by decomposition products.

EXAMPLE 22

Preparation of N-Vinyloxycarbonyl-N-methylcyclohexylamine (a) Preparation of N-α-Chloroethoxycarbonyl-N-methylcyclohexylamine.

A solution of N-methylcyclohexylamine (22.1 g, 0.2 mol) in ether (10 cc) was added (20 min) to a stirred, cooled (0° C.) solution of α-chloroethyl chloroformate (ACE-Cl) (28.3 g, 0.2 mol) in ether (25 cc). The mixture was stirred for another hour at room temperature and then the solid was filtered off. Evaporation of the filtrate was followed by vacuum distillation; 19.9 g 93% yield of boiling point 101°–103° C. at 0.5 mm.

IR ($\mu$): 5.82 (vs); CCl$_4$.

$^1$H NMR ($\delta$): 6.55 (q,J=6), 4.2–3.5 (m) 2.80 (s), 2.2–0.9 (m with d at 1.80); ratio 1:1:3:13; CCl$_4$.

MS (m/e): 221.0995 (P[$^{37}$Cl], 5%, Calc. 221.0997), 219.1024 (P[$^{35}$Cl], 16%, Calc. 219.1026), 156.1028 (P—CHClCH$_3$, 93%, Calc. 156.1024), 114 (73%), 70 (68%), 63 (94%), 55 (74%), 42 (100%).

(b) Dehydrohalogenation to N-VOC-N-Methylcyclohexylamine.

A stirred solution of N-ACE-N-methylcyclohexylamine (5.49 g, 0.025 mol) prepared in Ex 22a, 2,4,6-collidine (4.97 g, 0.041 mol), and bromobenzene (12 cc) was heated (oil bath at 170° C.) for 1.5 hours (in an earlier analytical scale reaction, product was formed in 90% yield and 10% decomposition products were present after 2 hours, NMR analysis). After the standard extraction workup, the product was isolated by vacuum distillation; bp 81°–85° C. at 0.2 mm.(R. C. Schnur, Ph.D. Thesis, The Pennsylvania State University (1973),reported 119° C. at 14 mm). The product (4.09 g) was contaminated by ca. 12% starting material (corrected absolute yield 78%, NMR analysis).

IR ($\mu$): 5.84 (vs), 6.06 (m); CCl$_4$.

$^1$H NMR ($\delta$): 7.19 (d of d, J=14,6), 4.65 (d of d, J=14,1), 4.32 (d of d, J=6,1), 4.2–3.6 (m), 2.81 (s), 2.1–0.8 (m); ratio 1:1:1:1:3:10; CCl$_4$.

In another experiment, a stirred solution of N-ACE-N-methylcyclohexylamine (10.4 g, 0.047 mol), (−)-β-pinene (8.1 g, 0.06 mol, bp 165°–167° C.), and o-dichlorobenzene (25 cc) was heated (oil bath at 185° C.) for 6 hours. Fractional vacuum distillation yielded 3.44 g of N-VOC-N-methylcyclohexylamine (40% yield; NMR pure) of bp 90°–92° C. at 0.6 mm. The residue remaining in the distillation pot was identified (NMR) as N-methylcyclohexylamine hydrochloride (ca. 58% recovered).

In a test of β-pinene as both a solvent and acid scavenger, a solution of N-ACE-N-methylcyclohexylamine in (−)-β-pinene, (ratio 1:4.6 equiv) was heated at 170° C. for 1.5 hours. By NMR analysis (1,1,2,2-tetrachloroethane as quantitative internal standard), the mixture was identified as 64% remaining starting material and 34% VOC-product.

EXAMPLE 23

Preparation of N,N-Diethyl O-Vinyl Carbamate (VOC-Diethylamine)

(a) Synthesis of N,N-Diethyl O-α-Chloroethyl Carbamate.

Triethylamine (17.6 g, 0.17 mol) in 25 cc dichloroethane was added slowly to a stirred, cooled (0° C.) solution of ACE-Cl (30.3 g, 0.21 mol), in dichloroethane (75 cc). The solution was refluxed for one hour after which the solvent was removed and the product isolated by vacuum distillation; 29.8 g, (96% yield, NMR pure) of boiling point 83°–89° C. at 11 mm.

IR ($\mu$): 5.81 (vs); neat.

$^1$H NMR ($\delta$): 6.58 (q, J=6), 3.30 (q, J=7), 1.80 (d, J=6), 1.13 (t, J=7); ratio 1:4:3:6; CCl$_4$.

MS (m/e): 181.0688 (P[$^{37}$Cl], 7%, Calc. 181.0683), 179.0712 (P[$^{35}$Cl], 21%, Calc. 179.0713), 166.0436 (P[$^{37}$Cl]—Me, 13% Calc. 166.0448), 164.0471 (P[$^{35}$Cl]—Me, 41%, Calc. 164.0478), 116.0709 (P—CHClCH$_3$, 30%, Calc. 116.0711), 102.0551 (P—C$_3$H$_6$Cl, 39%, Calc. 102.0555), 100.0764 (P—OCHClCH$_3$, 96%, Calc. 100.0763), 72.0816 (Et$_2$N, 50%, Calc. 72.0813), 65 (32%), 63 (100%), 58 (82%).

(b) N,N-Diethyl O-α-Bromoethyl Carbamate.

This bromo analogue of the above α-chloroethyl carbamate had a boiling point of 63°–66° C. at 0.7 mm and the spectral data listed below.

IR ($\mu$): 5.78 (vs); CCl$_4$.

$^1$H NMR ($\delta$): 6.69 (q, J=6), 3.24 (q,J=7), 1.97 (d, J=6), 1.12 (t, J=7); ratio 1:4:3:6; CCl$_4$.

MS (m/e): 225.0227 (P[$^{81}$Br], 3%, Calc. 225.0188), 223.0214 , (P[$^{79}$Br], 3%, Calc. 223.0208), 166 (11%), 164 (11%), 144 (18%), 109 (40%), 107 (39%), 101 (19%), 100 (100%), 72, (86%).

(c) Dehydrohalogenation .

1. Conversion of N,N-Diethyl O-α-Bromoethyl Carbamate to VOC-Diethylamine.

An oil bath containing a flask with a stirred sclution of CH$_3$CHBrOC(=O)NEt$_2$ (9.6 g, 0.043 mol), 2,4,6-collidine (6.6 g, 0.055 mol), tetrabutylammonium bromide (0.73 g, 0.002 mol), and tetrachloroethylene (18 cc, bp 121° C.) was heated at 125° C. for 1.5 hours (by NMR analysis, the reaction was actually finished after about 1 hour). After the standard extraction workup and distillation removal of volatiles, the product, VOC-NEt$_2$ was isolated by distillation at reduced pressure; 5.6 g (92% yield, NMR pure) of bp 97°–98° C. at 62 mm . The spectral properties of the product match those reported by Schnur; R. C. Schnur, Ph.D. Thesis, The Pennsylvania State University (1973). Schnur reported a boiling point of 63° C. at 13 mm.

$^1$H NMR ($\delta$): 7.20 (d of d, J=7,14), 4.65 (d of d, J=14,1), 4.31 (d of d, J=7,1), 3.29 (q, J=7), 1.12 (t, J=7); ratio 1:1:1:4:6; CCl$_4$.

In another experiment, a solution of the same bromoethyl carbamate (12.7 g, 0.057 mol), 2,4,6-collidine (8.5 g, 0.070 mol), tetra-n-hexylammonium chloride (1.25 g, 0.003 mol), and trichloroethylene (23 cc) was heated at 95° C. for 5 hours (reaction 90% complete after 2 hours). The product distillation fraction (NMR pure) contained 3.81 g (47% yield) of bp 91°–93° C. at 52 mm.

In an experiment performed in 1,2-dichloroethane at 95° C. and using collidine and Bu$_4$N$^+$ Br$^-$ as promoters, the estimated yield (NMR) of VOC—NEt$_2$ was 26% after 2.5 hours.

2. Conversion of N,N-Diethyl O-α-Chloroethyl Carbamate to VOC-Diethylamine.

The reaction of CH$_3$CHClOC(=O)NEt$_2$ was slower than from the α-bromo compound as is evident from the following experiment. When ACE-NEt$_2$ was substituted for the bromo analogue in the first experiment of this series, only 15% VOC-NEt$_2$ was formed after 2 hours at 125° C. in tetrachloroethylene and 85% of the starting ACE-NEt₂ remained (NMR analysis). With longer reaction times, however, the product yield increased.

EXAMPLE 24

Preparation of N,N-Dimethyl O-vinyl Carbamate (VOC-Dimethylamine)

(a) Preparation of ACE-Dimethylamine.

The substance was prepared by N-demethylation of trimethylamine with ACE-Cl in dichloroethane; boiling point 82°–84° C. at 17 mm.

IR($\mu$): 5.81 (vs); CCl₄.

¹H NMR ($\delta$): 6.57 (q, J=6), 2.93 (s), 1.80 (d, J=6); ratio 1:6:3; CCl₄.

MS (m/e): 153.0379 (P[$^{37}$Cl], 3%, Calc. 153.0370), 151.0399 (P[$^{35}$Cl], 11%, Calc. 151.0400), 89 (17%), 88 (20%), 72.0447 (P—OCHClCH₃, 100%, Calc. 72.0449), 65 (12%), 63 (38%).

(b) Conversion of ACE-Dimethylamine to VOC-Dimethylamine.

A solution of ACE-dimethylamine (7.84 g, 0.052 mmol), 2,4,6-collidine (7.54 g, 0.062 mol), and 20 cc of N,N,N',N'-tetraethylsulfamide (Et₂NSO₂NEt₂, dried over 4 Å sieves) was heated at 155° C. for 30 minutes when NMR analysis indicated that the reaction was 80% complete. The lower boiling point product was separated from the higher boiling solvent and salts by vacuum distillation. The fraction of boiling point 66°–71° C. at 30 mm contained VOC-NMe₂ in 32% absolute yield contaminated by collidine and a little ACE-NMe₂ and Et₂NSO₂NEt₂. The impurities were removed by refluxing the product with 10 cc of MeOH for 30 minutes. Ether, 40 cc, was added and the organic layer washed with 1N H₂SO₄, brine, the aqueous layers were backwashed with ether, dried (Na₂SO₄), rotoevaporated, and distilled to give pure VOC-NMe₂, boiling point 57°–61° C. at 26 mm; reported by Olofson, Schnur and Bunes, U.S. Pat. No. 3,905,981; 43° C. at 10 mm.

IR ($\mu$):5.78 (vs), 6.08 (m); CCl₄.

¹H NMR ($\delta$): 7.13 (d of d, J=14, 6), 4.65 (d of d, J=14, 1), 4.30 (d of d, J=6,1), 2.91 (s); ratio 1:1:1:6; CCl₄.

In two NMR test experiments, the reaction was performed for 30 minutes at 170° C. and for 1 hour at 140° C., respectively. In the first test, 57% of the product was formed, but the remainder had decomposed. In the second test, most of the starting material remained, but 26% VOC-NMe₂ was present and 9% decomposition was observed.

EXAMPLE 25

Preparation of N-Vinyloxycarbonyl-N-methyl-p-chloroaniline (N-VOC-N-methyl-p-chloroaniline (a) Preparation of N-ACE-N-Methyl-p-chloroaniline.

N-Methyl-p-chloroaniline (Aldrich, 94%), (19.9 g, 0.13 mol) and pyridine (10.5 g, 0.13 mol) were added to a cooled (0° C.), stirred solution of ACE-Cl (21.0 g, 0.15 mol) in 25 cc of ether. The mixture was stirred at room temperature for 1 hour and then passed through a silica gel plug using ether as the eluant. The eluate was evaporated in vacuo and the remaining viscous yellow oil was kept under vacuum (1 mm) overnight to remove volatiles. The product (32.3 g, 99% yield) was pure by NMR analysis.

IR ($\mu$): 5.78 (vs), 6.25 (w), 6.68 (m); CCl₄.

¹H NMR ($\delta$): 7.6–7.0 (m with large spike at 7.23), 6.52 (q, J=6), 3.26 (s), 1.69 (d, J=6); ratio 4:1:3:3; CCl₄.

MS (m/e): 251.0104 (P[$^{37}$Cl₂], 4%, Calc. 251.0108), 249.0142 (P[$^{37}$Cl$^{35}$Cl], 26%, Calc. 249.0137), 247.0177 (P[$^{35}$Cl₂], 42%, Calc. 247.0166), 185 (48%), 168 (53%), 140 (69%), 63 (100%).

(b) Conversion of N-ACE-N-Methyl-p-chloroaniline to N-VOC-N-Methyl-p-chloroaniline.

A solution of N-ACE-N-methyl-p-chloroaniline (10.8 g, 0.044 mol), (−)-$\beta$-pinene (9.4 g, 0.069 mol), and 27 cc of o-dichlorobenzene was heated (oil bath at 185° C.) for 9 hours, (by NMR analysis, the elimination was 22% complete after 3 hours), then cooled, and vacuum distilled. The distillation fraction of boiling point 75°–95° C. at 0.4 mm contained N-VOC-N-Methyl-p-chloroaniline (absolute yield 40%) contaminated by much N-methyl-p-chloroaniline. The amine was removed by extraction with aqueous H₂SO₄. Analytically pure N-VOC-N-methyl-p-chloroaniline had a boiling point of 93°–95° C. at 0.3 mm.

IR ($\mu$): 5.76 (vs), 6.05 (m), 6.67 (s); CCl₄.

¹H NMR ($\delta$): 7.5–7.0 (m with large spike at 7.20), 4.61 (d of d, J=14,1), 4.36 (d of d, J=6,1), 3.22 (s); ratio 5:1:1:3; CCl₄.

MS (m/e): 213.0372 (P[$^{37}$Cl], 9%, Calc. 213.0370), 211.0402 (P[$^{35}$Cl], 30%, Calc. 211.0400), 170 (31%), 168 (100%).

EXAMPLE 26

Preparation of N-Vinyloxycarbonyl-14-Acetylnoroxycodone. (N-VOC-14-acetyl-noroxycodone)

(a) Preparation of N-ACE-14-Acetylnoroxycodone.

ACE-Cl (4.6 g, 32 mmol) in 5 cc of 1,2-dichloroethane was added to a cooled (0° C.), stirred solution of 14-acetyloxycodone (2.0 g, 5.7 mmol), 1,8-bis(dimethylamino)naphthalene (0.2 g, 1.0 mmol), and 15 cc of dichloroethane. The mixture was left at room temperature for 1 hour and then stirred overnight at 85° C. Anhydrous HCl was bubbled into the cooled solution for 2 minutes and then the solvent and excess ACE-Cl were removed in vacuo. Charcoal and dichloromethane were added and the mixture was passed through a silica plug (CH₂Cl₂:MeOH 95:5 as eluant). Vacuum evaporation of the solvent afforded NMR pure N-ACE-14-acetylnoroxycodone as a yellowish foam, 2.1 g, (83% yield).

IR ($\mu$): 5.65–5.9 (vs with maxima at 5.72 and 5.83); CH₂Cl₂.

¹H NMR ($\delta$): 7.0–6.3 (m), 5.8–5.5 (broad), 4.65 (s), 4.2–3.8 (m with methyl spike at 3.90), 3.4–1.3 (m with methyl s at 2.17 and methyl d at 1.84); ratio 3:1:1:4:15; CDCl₃.

The product N-ACE-14-acetylnoroxycodone has the structure hereinbelow:

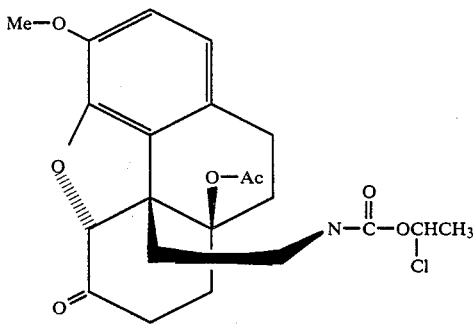

(b) Conversion of N-ACE-14-Acetylnoroxycodone to N-VOC-14-Acetylnoroxycodone.

A solution of N-ACE-14-acetylnoroxycodone (2.1 g, 4.6 mmol) and 2,4,6-collidine (1.2 g, 10.1 mmol) in 4.8 cc of bromobenzene was heated (oil bath at 170° C.) for 3 hours. Methanol, 5 cc, was added to the cooled, red solution which then was refluxed for 30 minutes. The mixture was diluted with methylene chloride, washed with 1N $H_2SO_4$, and dried ($Na_2SO_4$). Charcoal was added and the slurry was passed through a silica gel plug using ethyl acetate as the eluant. Vacuum evaporation afforded N-VOC-14-acetylnoroxycodone as a light yellow solid, 0.96 g (51% yield). After recrystallization from $CH_2CL_2$-heptane and from methanol, the product has a melting point of 180°-182° C.; reported by Olofson and Pepe, U.S. Pat. No. 4,141,897: 181°-182.5° C., 182.5°-183.5° C. The IR and NMR spectral data for the product were in accord with the values reported by Olofson and Pepe, loc cit.

EXAMPLE 27

Preparation of N-Vinyloxycarbonyl-guvacoline. (N-VOC-Guvacoline)

(a) Preparation of N-ACE-Guvacoline.

Freshly distilled (2.08 g, 0.0134 mol)arecoline in 8 cc of dichloroethane was dripped (10 minutes) into a stirred solution (−5° C.) of ACE-Cl (2.59 g, 0.0181 mol) and 1,8-bis-(dimethylamino)-naphthalene (0.28 g, 0.00131 mol) in 10 cc of dichloroethane. The solution first was warmed to room temperature and then to reflux, during which time, a white solid precipitated. After refluxing 30 minutes, the now reddishorange mixture was cooled, anhydrous HCl slowly was bubbled (2 minutes) through the mixture, which dissolved the solid, and the solution was passed through a silica gel plug (1"×1"), methylene chloride being used as the eluant. Rotary evaporation of the total eluant, (125 cc), afforded 3.20 g (96% yield) of crude N-ACE-guvacoline as a gold oil.

IR ($\mu$): 5.81 (vs), 6.10 (w); $CH_2Cl_2$.

NMR ($\delta$): 7.3-6.8 (m), 6.58 (q, J=6), 4.4-3.9 (m), 3.8-3.2 (m with methyl spike at 3.73), 2.6-2.1 (m), 1.83 (d, J=6); ratio 1:1:2:5:2:3; $CDCl_3$.

(b) Conversion of N-ACE-Guvacoline to N-VOC-Guvacoline.

A solution of N-ACE-guvacoline (1.65 g, 6.66 mol), 2,4,6-collidine (1.09 g, 8.99 mmol), and 3.2 cc of bromobenzene was heated (oil bath at 170° C.) for 6.5 hours. Methanol was then added to the cooled solution which was subsequently refluxed for 30 minutes. Ether (20 cc) was added to the cooled solution which was extracted with 1N $H_2SO_4$ (3×15 cc) and 10 cc of brine. The aqueous layers were backwashed with ether (2×10 cc) and the combined organic phases were dried ($Na_2SO_4$), rotoevaporated, and vacuum distilled to give N-VOC-guvacoline, 0.842 g, (60% yield) of boiling point 120°-122° C. at 0.6 mm; R. A. Olofson, R. C. Schnur, and L. A. Bunes, U.S. Pat. No. 3,905,981,reported 132° C. at 0.8 mm, 104°-106° C. at 0.2 mm).

IR ($\mu$): 5.78 (vs), 6.02 (w), 6.06 (m); $CCl_4$.

$^1$H NMR ($\delta$): 7.4-6.85 (m including d of d, J=14, 7, at 7.15), 4.71 (broad d, J=14), 4.39 (d of d, J=7,1), 4.3-4.0 (m), 3.70 (s), 3.53 (t, J=6), 2.6-2.1 (m); ratio 2:1:1:2:3:2:2; $CCl_4$.

N-VOC-Guvacoline is:

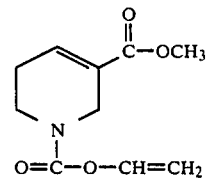

EXAMPLE 28

Preparation of N-Vinyloxycarbonyl-O-Acetylnortropine (N-VOC-O-Acetyl Nortropine)

(a) Preparation of N-ACE-O-Acetylnortropine.

N-Demethylation of O-acetyltropine with ACE-Cl using the procedure already described for the similar demethylation of arecoline afforded N-ACE-O-acetyl-nortropine as a yellow oil after vacuum evaporation of the chromatography eluate.

IR ($\mu$): 5.81 (vs); $CH_2Cl_2$.

NMR ($\delta$):6.60 (q, J=6), 5.2-4.9 (m), 4.5×4.1 (m), 2.5-1.6 (m with methyl s at 2.03 and methyl d at 1.80); ratio 1:1:2:14; $CDCl_3$.

(b) Conversion of N-ACE-O-Acetylnortropine to N-VOC-O-acetylnortropine.

A solution of N-ACE-O-acetylnortropine (4.39 g, 0.016 mol) and 2,4,6-collidine (2.36 g, 0.020 mol) in 7.5 cc of bromobenzene was heated (oil bath at 170° C.) for 3.5 hours. In an earlier NMR scale experiment, 73% of product had formed after 2 hours. The solution was cooled to ca. 50° C., diluted with 10 cc of methanol and stirred at this temperature for 45 minutes. The cooled solution was diluted with 40 cc of ether, washed with 1 N $H_2SO_4$ (3×25 cc) and brine (15 cc). The aqueous layers were back extracted with ether (2–20 cc). The combined organic phases were dried ($Na_2SO_4$), roto-evaporated, and vacuum distilled. N-VOC-O-Acetyl-nortropine was isolated as a colorless oil, 3.26 g, (86% yield, NMR pure) of boiling point 125°-127° C. at 0.6 mm.

IR ($\mu$): 5.73 (vs), 5.80 (vs), 6.06 (m); $CCl_4$.

$^1$H NMR ($\delta$): 7.17 (d of d, J=14, 7), 5.2-4.8 (m), 4.65 (d of d, J=14, 1), 4.5-4.1 (m with d of d at 4.35), 2.4-1.5 (m with methyl s at 1.98); ratio 1:1:1:3:11; $CCl_4$.

The structure of N-VOC-O-Acetylnortropine is:

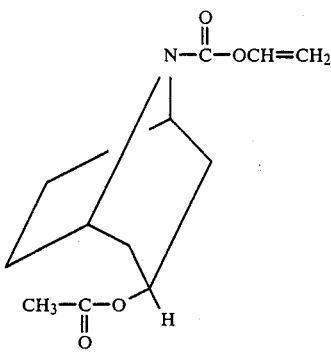

EXAMPLE 29

Preparation of
E,Z-N-(3-Chloropropenyloxycarbonyl)-N,N-diisopropylamine (a) Preparation of N-(1,3-dichloropropyloxycarbonyl)-N,N-diisopropylamine.

Diisopropylamine (9.4 g, 0.093 mol) in 15 cc of ether was added over 20 minutes to a cooled (15° C.), stirred solution of 1,3-dichloropropyl chloroformate (boiling point 65°–68° C. at 10 mm, 7.1 g, 0.037 mol) in 40 cc of ether. After stirring for 30 minutes at room temperature, the precipitated salts were filtered off; the solvent was evaporated and the product was isolated by vacuum distillation; boiling point 88°–92° C. at 0.3 mm; 8.29 g (87% yield). The product has the formula ClCH$_2$CH$_2$CHCl—OC(=O)—N(CHMe$_2$)$_2$.

IR ($\mu$): 5.79 (vs); CCl$_4$.

$^1$H NMR ($\delta$): 6.64 (t, J=6), 4.3–3.4 (m, with t of J=7 at 3.65), 2.46 (q with broad center peaks, J=6, 7), 1.20 (d, J=7); ratio 1:4:2:12; CCl$_4$.

MS (m/e): 259 (1%) 257.0751 (P[$^{37}$Cl$^{35}$Cl], 6%, Calc. 257.0763), 255.0793 (P[$^{35}$Cl$_2$], 8%, Calc. 255.0793), 244 (9%), 242 (54%), 240 (87%), 144 (15%), 130 (33%), 128 (45%), 43 (100%).

(b) Preparation of E,Z-N-(3-Chloropropenyloxycarbonyl)N,N-diisopropylamine

A flask containing a solution of ClCH$_2$CH$_2$CHCl—OC(=O)—N(CHMe$_2$)$_2$ (8.0 g, 0.031 mol), 2,4,6-collidine (4.6 g, 0.038 mol), and tetrabutylammonium bromide (0.76 g, 0.002 mol) in 17 cc of tetrachloroethylene was refluxed in an oil bath maintained at 125° C. (By NMR analysis, the reaction was 41% complete after 3 hours). The reaction was continued for a total of 5 hours, the mixture diluted with 40 cc of ether and then extracted with 1N H$_2$SO$_4$ (3×30 cc) and brine (20 cc). The aqueous layers were back extracted with ether (2×20 cc). The combined organic layers were dried (Na$_2$SO$_4$), rotary evaporated, and vacuum distilled. The fraction of boiling point 98°–99° C. at 0.4 mm (4.67 g) contained the E and Z geometrical isomers of the product, 3-(chloropropenylocarbonyl)-N,N-diisopropylamine in a yield of 56% and an E:Z ratio of 1:1.7. Based on NMR analysis, the product also was contaminated by 16 mol % of the starting dichloropropyl carbamate. By using longer reaction times, the product could be obtained free of this reactant. The spectral data for the pure E,Z-product are given below. The compound has the formula ClCH$_2$CH=CHOC(=O)N(CHMe$_2$)$_2$.

IR($\mu$): 5.81 (s), 5.99 (w); CCl$_4$.

$^1$H NMR ($\delta$): 7.42 (d, E-isomer, J=12), 7.20 (d, Z-isomer, J=6), 5.7–4.7 (m), 4.3–3.4 (m), 1.33–1.18 (overlapping d of J=6 at 1.27 and d of J=6 at 1.23); ratio 0.37:0.63:1:4:12; CCl$_4$.

MS (m/e): 221(P[$^{37}$Cl ], 1%), 219.1031 (P[$^{35}$Cl], 3%, Calc. 219.1026), 128 (61%), 86 (81%), 43 (100%).

This experiment demonstrates that the elimination of the chlorine in the 1-position is surprisingly possible while the chlorine atom in the 3-position is not attacked.

EXAMPLE 30

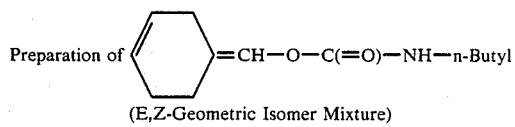

(E,Z-Geometric Isomer Mixture)

(a)

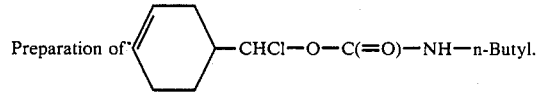

n-Butylamine (13.5 g, 0.18 mol) in 10 cc of ether was added over a 30 minute period to a stirred, cooled (0° C.) solution of (3-cyclohexenyl)-chloromethyl chloroformate (made by the general process described in European application No. 40153, boiling point 81°–83° C. at 1 mm) (16.6 g, 0.080 mol) in 25 cc of ether. The mixture was stirred at room temperature for one hour, anhydrous HCl was bubbled through the mixture for 2 minutes, the salts filtered off and charcoal was added to the filtrate which was then evaporated at reduced pressure. The residue was passed through a silica gel plug (2"×2") using 1:1 dichloromethane-ethyl acetate as the eluant. Vacuum evaporation afforded 16.8 g (86% yield) of the product whose structure is pictured in the title as an orange oil. The product could not be vacuum distilled without decomposition initiated by the HCl elimination process described below.

IR ($\mu$): 5.70 (vs); CCl$_4$.

$^1$H NMR ($\delta$): 6.5–6.1 (m), 5.9–5.3 (m), 3.15 (broad q, J=6), 2.9–0.6 (m); ratio 1:3:2:14; CCl$_4$.

MS (m/e): 247.1143 (P[$^{37}$Cl], 1%, Calc. 247.1153), 245.1181 (P[$^{35}$Cl], 3%, Calc. 245.1182), 128 (24%), 118 (100%).

(b)

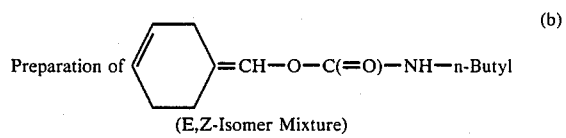

(E,Z-Isomer Mixture)

A flask containing a sample of the product chloroalkyl carbamate from Example 30a (5.0 g, 0.02 mol) was stirred neat at 125° C. under a vacuum of 50 mm (no reflux condenser) for four hours. The remaining liquid was chromatographed on a 1"×8" silica gel column using dichloromethane as the eluant. Vacuum evaporation of the eluate afforded 0.92 g (21% yield, NMR pure, tlc: single spot of R$_f$0.48 on silica developed with CH$_2$Cl$_2$) of the product (pair of geometrical isomers) whose structure is pictured in the title as a yellow oil.

IR ($\mu$): 2.90 (m, NH stretch), 5.79 (vs, C=O stretch), 5.8–5.95 (m to w absorptions, C=C stretches); CH$_2$Cl$_2$.

$^1$H NMR ($\delta$): 7.1–6.6 (broad s), 5.8–5.4 (broad s), 5.4–4.8 (broad s), 3.5–0.6 (m); ratio 1:2:1:13; CDCl$_3$.

MS (m/e): 209.1423 (P, 5%, Calc. 209.1416), 128 (44%), 110 (100%), 86 (73%).

The Chemical Abstracts Service name given for the structure pictured in the title of Example 30b (and therefore of the product of the process described in Example 30b) is: Carbamic acid, butyl-, 3-cyclohexen-1-ylidenemethyl ester.

EXAMPLE 31

Preparation of E,Z-N-(3-Methyl-1-butenyloxycarbonyl)-N-(4-chlorobutyl)-N-ethylamine (a) Preparation of N-(1-Chloro-3-methylbutyloxycarbonyl)-N-(4-chlorobutyl)-N-ethylamine.

A solution of N-ethylpyrrolidine (7.1 g, 0.071 mol) in 15 cc of 1,2-dichloroethane was added over 15 minutes to a stirred, cooled (0° C.) solution of 1-chloro-3-methylbutyl chloroformate (made from isovaleraldehyde by the general process described in European application No. 40153, boiling point 74°–76° C. at 30 mm) (11.1 g, 0.06 mol) in 25 cc of dichloroethane also containing 1,8-bis-(dimethylamino)-naphthalene (0.94 g, 0.004 mol). The mixture was refluxed for 30 minutes, then cooled, and anhydrous HCl was bubbled slowly through the solution for 2 minutes. Rotoevaporation of the solvent afforded a residue from which the product was isolated and purified by chromatography through a silica gel column (6"×1") using ethyl acetate as the eluant. Vacuum evaporation of the eluate gave a yellow oil, 16.4 g (96% yield) identified as the product, $(CH_3)_2CHCH_2$—CHCl—OC(=O)—N(CH$_2$CH$_3$)—CH$_2$CH$_2$CH$_2$CH$_2$Cl; boiling point of 119°–122° C. at 0.4 mm.

IR ($\mu$): 5.82 (vs); CH$_2$Cl$_2$.

$^1$H NMR ($\delta$): 6.47 (t, J=6), 3.7–2.9 (m), 2.1–1.3 (m), 1.20–0.82 (overlapping t of J=7 at 1.05 and d of J=6 at 0.87); ratio 1:6:7:9; CDCl$_3$.

MS (m/e): 287.1052 (P[$^{37}$Cl$_2$], 0.2%, Calc. 287.1047), 285.1106 (P[$^{37}$Cl$^{35}$Cl], 1%, Calc. 285.1077), 283.1119 (P[$^{35}$Cl$_2$], %, Calc. 283.1106), 206 (51%), 102 (51%), 69 (100%).

(b) Preparation of E,Z-N-(3-Methyl-1-butenyloxycarbonyl)-N-(4-chlorobutyl)-N-ethylamine.

A mixture of N-(1-chloro-3-methylbutyloxycarbonyl)-N-(4-chlorobutyl)-N-ethylamine (6.32 g, 0.022 mol), 2,4,6-collidine (3.32 g, 0.027 mol), and tetrabutylammonium bromide (0.55 g, 0.002 mol) in 10 cc of tetrachloroethylene was refluxed for 12 hours. (By NMR analysis, the reaction was 43% complete after one hour.) The cooled mixture then was poured onto a 1"×6" silica gel chromatography column and eluted with ethyl acetate. Vacuum evaporation of the eluate afforded the purified product as a yellow oil; 5.20 g (94% yield). Vacuum distillation of the product (boiling point of 111°–114° C. at 0.4 mm) removed the color but did not otherwise change the purity. The ratio of cis to trans isomers in the product, $(CH_3)_2CHCH=CH$—OC(=O)—N(CH$_2$CH$_3$)—CH$_2$CH$_2$CH$_2$CH$_2$Cl, was determined by NMR analysis (Z:E=4:3) and was the same both before and after the distillation step.

IR ($\mu$): 5.81 (vs), 5.95 (m); CCl$_4$.

$^1$H NMR ($\delta$): 7.2–6.7 (m), 5.25 (d of d, J=12, 7, E-isomer), 4.60 (d of d, J=9, 6, Z-isomer), 3.6–3.0 (m), 2.7–1.3 (m), 1.30–0.97 (overlapping t of J=7 at 1.15 and d of J=7 at 1.00); ratio 1:0.43:0.57:6:5:9; CDCl$_3$.

MS (m/e): 249.1337 (P[$^{37}$Cl], 2%, Calc. 249.1310), 247.1338 (P[$^{35}$Cl], 5%, Calc. 247.1339), 164 (9%), 162 (29%), 93 (32%), 91 (100%).

This experiment demonstrates that elimination of H—Cl from an N-(1-chloroalkoxycarbonyl)-amine to give the derived N-(1-alkenyloxycarbonyl)-amine is surprisingly possible while another chlorine atom attached to another chloroalkyl substituent (here a 4-chlorobutyl group) on the same nitrogen is not attacked.

EXAMPLE 32

Preparation of N,N'-di-(3-Methylbutenyloxycarbonyl)N,N'-dimethyl-1,3-propanediamine (a) Preparation of N,N'-di-(1-Chloro-3-methylbutyloxycarbonyl)-N,N'-dimethyl-1,3-propanediamine.

Reaction of N,N,N',N'-tetramethylpropanediamine (6.86 g, 0.053 mol) with 1-chloro-3-methylbutyl chloroformate (17.7 g, 0.096 mol) in dichloroethane (total of 40 cc) in the presence of 1,8-bis(dimethylamino)-naphthalene (1.2 g, 0.006 mol) as described in Example 31a followed by workup of the reaction mixture and the chromatographic purification of the product also as described in Example 31a afforded, after vacuum evaporation of the eluate, 15.6 g (82% yield, NMR pure) of the product, $(CH_3)_2CHCH_2$—CHCl—OC(=O)—N(CH$_3$)—(CH$_2$)$_3$—(CH$_3$)N—C(=O)O—CHCl—CH$_2$CH(CH$_3$)$_2$, as a yellow oil.

IR ($\mu$): 5.82 (vs); CH$_2$Cl$_2$.

$^1$H NMR ($\delta$): 6.47 (broad t, J=6), 3.29 (broad t, J=7), 2.92 (s), 2.2–1.5 (m), 0.93 , (d, J=6); ratio 2:4:6:8:12; CDCl$_3$.

MS (m/e): 400.1744 (P[$^{37}$Cl$^{35}$Cl], 0.5%, Calc. 400.1709), 398.1762 (P[$^{35}$Cl$_2$], 1%, Calc. 398.1739), 277 (8%), 154 (14%), 128 (100%).

(b) Preparation of N,N'-di-(3-Methylbutenyloxycarbonyl)N,N'-dimethyl-1,3-propanediamine.

A solution of N,N'-di-(1-chloro-3-methylbutyloxycarbonyl)-N,N'-dimethyl-1,3-propanediamine (6.19 g, 0.016 mol), 2,4,6-collidine (4.4 g, 0.036 mol), and tetrabutylammonium bromide (0.65 g, 0.002 mol) in 13 cc of tetrachloroethylene was refluxed for 12 hours. (A smaller scale rection was 44% complete after one hour; NMR analysis.) The mixture was cooled, poured onto a silica gel column (6"×1"), and chromatographed with ethyl acetate as the eluant. Vacuum evaporation of the eluate afforded a tan oil, 4.70 g (93% yield, NMR pure), identified as the product, $(CH_3)_2CHCH=CH$—OC(=O)—N(CH$_3$)—(CH$_2$)$_3$—(CH$_3$)N—C(=O)O—CH=CHCH(CH$_3$)$_2$. Based on NMR analysis, the geometries at the two carbon to carbon double bonds were 43% trans and 57% cis. Thus, the calculated geometric isomer mixture is 18% EE, 49% EZ, and 32% ZZ assuming no long distance interactions. Based on the isomer ratio found in Example 31b, such a long distance interaction would be extremely unlikely. Slight product decomposition (NMR analysis) occurred on vacuum distillation; boiling point of 163°–171° C. at 0.4 mm.

IR ($\mu$): 5.81 (vs), 5.96 (m); CCl$_4$.

$^1$H NMR ($\delta$): 7.2–6.7 (m), 5.25 (d of d, J=12, 7, E-geometry), 4.58 (d of d, J=9, 6, Z-geometry), 3.32 (broad t, J=7), 2.96 and 2.93 (overlapping singlets for different N-Me conformations), 2.7–1.5 (m), 1.00 (d, J=6); ratio 2:0.86:1.14:4:6:4:12; CDCl$_3$.

MS (m/e): 326.2210 (P, 3%, Calc. 326.2206), 241 (35%), 184 (44%), 129 (100%).

EXAMPLE 33

Preparation of N,N'-Di-(3-Methylbutenyloxycarbonyl)-1,10-diaza-18-crown-6

(a) Preparation of N,N'-Di-(1-Chloro-3-methylbutyloxycarbonyl)-1,10-diaza-18-crown-6.

A solution of 1-chloro-3-methylbutyl chloroformate (1.58 g, 8.54 mmol) in dichloromethane (10 cc) was added to a cooled (0° C.), stirred solution of 1,10-diaza-18-crown-6 (0.99 g, 3.75 mmol) and pyridine (0.68 g, 8.60 mmol) in dichloromethane (10 cc). The reaction mixture was warmed to room temperature, stirred for 1 hour, and poured onto a silica gel plug (eluted with ethyl acetate). Upon vacuum evaporation of the eluate and drying the residue in vacuo overnight, a clear oil remained; 1.78 g (85% yield, $^1$H NMR pure).

IR (μ): 5.82 (vs); $CH_2Cl_2$.

$^1$H NMR (δ): 6.50 (broad t, J=6), 3.60 (broad s), 2.2–1.6(m), 0.95 (broad d, J=6); ratio 2:24:6:12; $CDCl_3$.

MS (m/e): 562 (P[$^{37}Cl_2$], 0.2%), 560.2402 (P[$^{37}Cl^{35}Cl$], 0.8%, calc. 560.2444), 558.2452 (P[$^{35}Cl_2$], 1.2%, Calc. 558.2475), 351 (19%), 289 (11%), 158 (25%), 114 (100%).

(b) Preparation of N,N'-Di-(3-Methylbutenyloxycarbonyl)-1,10-diaza-18-crown-6.

A mixture of N,N'-di(1-chloro-3-Methylbutyloxycarbonyl)-1,10-diaza-18-crown-6 (0.64 g, 1.14 mmol), collidine (0.40 g, 3.30 mmol), and tetrabutylammonium bromide (0.055 g, 0.17 mmol) was refluxed in tetrachloroethylene (1.3 cc) for 8.5 hours. After pouring onto a silica gel plug and elution with ethyl acetate, 0.40 g of a yellow oil remained after drying the residue in vacuo at 80° C. overnight (71% yield, $^1$H NMR pure with an E:Z ratio of 0.68:1).

IR (μ): 5.81 (vs), 5.98 (m); $CCl_4$.

$^1$H NMR (δ): 7.2–6.8 (m), 5.26 (d of d, J=12, 7, E geometry), 4.63 (d of d, J=9, 6, Z-geometry), 3.60 (broad s), 2.8–2.0 (m), 1.02 (d, J=6); ratio 2:0.81:1.19:24:2:12; $CDCl_3$.

MS (m/e): 486.2907 (P, 3%, Calc. 486.2941), 401 (48%), 357 (95%), 114 (100%).

The structure of the product in (b) is:

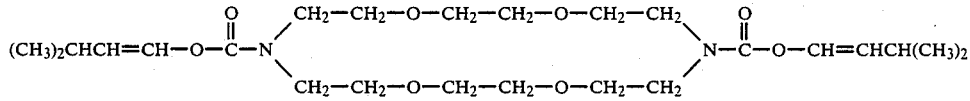

In a similar manner, 1,10-diaza-18-crown-6 is reacted with α-chloroethyl chloroformate (ACE-Cl) to give the intermediate N,N'-di-α-chloroethyl compound which is dehydrohalogenated similarly to Example 21b to give N,N'-di-(vinyloxycarbonyl)-1,10-diaza-18-crown-6.

EXAMPLE 34

Preparation of N-(Isobutenyloxycarbonyl)-N'-Methylpiperazine (a) Preparation of N-(α-Chloroisobutyloxycarbonyl)-N'-Methylpiperazine.

α-Chloroisobutyl chloroformate (9.51 g, 0.056 mol) in 15 cc of dichloroethane was added (20 minutes) to a cooled (−5° C.), stirred solution of N,N'-dimethylpiperazine (11.7 g, 0.102 mol) in 25 cc of dichloroethane. The reaction ixture was stirred at room temperature (1 hour) and then refluxed (30 minutes). After removal of the solvent, the product was purified by passage through a silica gel plug (ethyl acetate as eluant). Upon evaporation of the eluate, a yellow oil remained (later solidified on standing); 11.2 g (86% yield, $^1$H NMR pure).

IR (μ): 3.56 (w), 5.78 (vs); $CCl_4$.

$^1$H NMR (δ): 6.31 (d, J=5), 3.51 (t, J=5), 2.6–1.8 (m with t of J=5 at 2.36 and methyl s at 2.28), 1.05 (d, J=6); ratio 1:4:8:6; $CDCl_3$.

MS (m/e): 236.1113 (P[$^{37}Cl$], 6%, Calc. 236.1106), 234.1140 (P[$^{35}Cl$], 20%, Calc. 234.1135), 127 (73%), 70 (100%).

(b) Preparation of N-(Isobutenyloxycarbonyl)N'-methylpiperazine.

A mixture of N-(α-Chloroisobutyloxycarbonyl)-N'-methylpiperazine (10.6 g, 0.0452 mol) and tetrabutylammonium bromide (0.90 g, 0.003 mol) was heated neat for 3 hours at 125° C. and 1 mm. The mixture refluxed for ca. 15 minutes and then solidified. Water (15 ml) and 10 cc of dichloromethane were added to the cooled reaction vessel. Excess solid $K_2CO_3$ then was added slowly to the stirred mixture (to pH ≳11). The organic phase was separated and washed with 10% $K_2CO_3$ solution (50 cc). The combined aqueous extracts were washed with dichloromethane (2×20 cc) and the dichloromethane layers were combined, dried ($Na_2SO_4$), rotoevaporated, and vacuum distilled; 5.67 g (63% yield, $^1$H NMR pure) of bp 94°–99° C. at 0.7 mm.

IR (μ): 3.55 (w), 5.81 (vs); $CCl_4$.

$^1$H NMR (δ): 6.9–6.6 (m), 3.53 (t, J=5), 2.45–2.28 (overlapping t of J=5 at 2.34 and methyl s at 2.28), 1.63 (broad s); ratio 1:4:7:6; $CDCl_3$.

MS (m/e): 198.1364 (P, 26%, Calc. 198.1368), 127 (100%), 98 (9%), 70 (13%).

In another smaller scale reaction performed in the same manner, the product was purified by passing the residue (after aqueous $K_2CO_3$ workup and evaporation of solvent) through a silica gel plug (ethyl acetate as eluant). A yellow oil, with some white solid present, was isolated after rotoevaporation of the eluate (85% crude yield). The solid was triturated with hexane and a white solid remained (mp 149°–151° C.). Analysis of spectral data showed the by-product to be N,N'-di-(isobutenyloxycarbonyl) piperazine.

IR (μ): 5.85 (vs); $CH_2Cl_2$.

$^1$H NMR (δ): 6.78 (broad s), 3.53 (s), 1.63 (broad s); ratio 2:8:12; $CDCl_3$.

MS (m/e): 282.1567 (P, 18%, Calc. 282.1580), 211 (100%), 139 (26%), 55 (65%).

In a similar manner, N,N'-di-methylpiperazine is reacted with α-chloroethyl chloroformate (ACE-Cl) to give the intermediate N-α-chloroethoxycarbonyl N'-methyl piperazine, which is then dehydrohalogenated as in Example 21b to give N-(vinyloxycarbonyl)N'-methylpiperazine.

EXAMPLE 35

Preparation of N-3-[N'-(Isobutenyloxycarbonyl)-N'-Methylamino]propyltrimethylammonium Chloride.

(a) Preparation of (3-Dimethylaminopropyl)trimethylammonium Chloride.

(3-Dimethylaminopropyl)trimethylammonium iodide was made as described by Seeman and Bassfield in J. Org. Chem., 42, 2337 (1977); mp 171.5°–172.5° C. (lit mp 173.5°–174.5° C.); 3.76 g (13.8 mmol) was dissolved in 95% ethanol and passed through a column of ion exchange resin (Amberlite IRA-400 C. P., RN+Me$_3$ Cl$^-$, 35 g, 150.5 mmol) with 95% ethanol as the eluant. The eluate was rotoevaporated and the product (3-dimethylaminopropyl)trimethylammorium chloride was dried in vacuo at 80° C.; 2.48 g (99% yield) of a white powder (mp 146°–148° C.).

$^1$H NMR (δ): 3.9–3.4 (m with spike at 3.47), 2.6–1.7 (m with spike at 2.20); ratio 11:10; CDCl$_3$.

(b) Preparation of N-3-[N'-(α-Chloroisobutyloxycarbonyl)-N'-methylamino]propyltrimethylammonium Chloride.

A solution of α-chloroisobutyl chloroformate 2.40 g, 14.0 mmol) in 10 cc of dichloroethane was added (10 minutes) to a cooled (0° C.), stirred mixture of the 3-dimethylaminopropyltrimethylammonium chloride (2.48 g, 13.7 mmol) in 10 cc of dichloroethane. The reaction mixture was heated to 75° C. for 30 minutes, cooled, and filtered. The filtrate was concentrated and a light brown oil remained (3.94 g). Analysis ($^1$H NMR) showed that the product mixture contained N-3-[N'-(α-chloroisobutyloxycarbonyl)-N'-methylamino]propyltrimethylammonium chloride and some isobutenyl carbamate (2:1, respectively). The combined yield of the two carbamates was 95%. The spectra for the pure chloroisobutyl carbamate are given below.

IR (μ): 5.82 (vs); CH$_2$Cl$_2$.

$^1$H NMR (δ): 6.3–6.1 (m), 3.9–2.8 (m with N'+Me$_3$ spike at 3.47 and N-Me spike at 3.02), 2.5–1.8 (m), 1.09 (broad d, J=6); ratio 1:16:3:6; CDCl$_3$.

(c) Preparation of N-3-[N'-(Isobutenyloxycarbonyl)-N'-methylamino]propyltrimethylammonium Chloride.

The mixture from (b) above (3.81 g, 13.3 mmol) was-refluxed in 20 cc of dichloroethane. A piece of pH paper held over the CaCl$_2$ drying tube indicated that HCl gas was evolving from the heated mixture. After 4.5 hours, the reaction mixture was cooled and filtered. The gum remaining after the filtrate was concentrated was identified as the expected product ($^1$H NMR pure, 3.42 g, 97% yield) of structure:

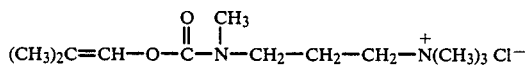

IR (μ): 5.84 (vs); CH$_2$Cl$_2$.

$^1$H NMR (δ): 6.65 (broad s), 4.2–2.8 (m with N'+Me$_3$ spike 3.45 and N-Me spike at 3.01), 2.6–1.9 (m), 1.65 (broad s); ratio 1:16:2:6; CDCl$_3$.

MS (m/e): 214.1680 (P-MeCl, 1.2%, Calc. 214.1681), 143 (23%), 84 (38%), 58 (100%).

In another experiment, the chloroisobutyl carbamate intermediate was not isolated. After demethylation of the 3-dimethylaminopropyltrimethylammonium chloride (4.17 g, 23.1 mmol) with chloroisobutyl chloroformate (5.50 g, 32.2 mol) in dichloroethane, followed by filtration and concentration of the filtrate (as before), the residue was heated to 70° C. at ca. 1 mm for 2 days. Analysis ($^1$H NMR) of the product mixture (5.62 g) showed a ratio of 4.4:1 of isobutenyl to chloroisobutyl carbamates, respectively (75% corrected yield).

Similarly, (3-dimethylaminopropyltrimethylammonium chloride is reacted with α-chloroethyl chloroformate (ACE-Cl) to give the intermediate α-chloroethyl compound which is then dehydrohalogenated as in Example 21B to give N-3-[N'-(vinyloxycarbonyl)-N'-methylamino]propyltrimethyl ammonium choride.

EXAMPLE 36

Preparation of N,N'-Di-VOC-N,N'-di-(2-methylaminoethyl) Carbonate (a) Prepration of N,N'-Di-ACE-N,N'-di-(2-methylaminoethyl) Carbonate.

A solution of ACE-Cl (12.6 g, 0.088 mol) in 15 cc of dichloroethane was added over 15 minutes to a cooled (0° C.) stirred solution of 2-dimethylaminoethyl carbonate (prepared as described by Angier et al, in J. Med. Chem., 11, 720 (1968)), (8.65 g, 0.042 mol) and Proton Sponge 0.35 g, 0.002 mol) in dichloroethane (25 cc). The reaction mixture was stirred at room temperature for 1 hour and then refluxed for 30 minutes. Anhydrous HCl was bubbled into the cooled mixture for 2 minutes and the solvent and excess ACE-Cl were removed in vacuo. A light yellow oil was obtained after the residue was passed through a silica gel plug (ethyl acetate as eluant) and the eluate was vacuum evaporated; 9.70 g (59% yield, $^1$H NMR pure).

IR (μ): 5.70 (s), 5.78 (vs); CCl$_4$.

$^1$H NMR (δ): 6.43 (q, J=6), 4.19 (broad t, J=5), 3.49 (broad t, J=5), 2.95 (s), 1.77 (d, J=6); ratio 2:4:4:6:6; CDCl$_3$.

(b) Preparation of N,N'-Di-VOC-N,N'-di-(2-methylaminoethyl) Carbonate.

A mixture of N,N'-di-ACE-N,N'-di-(2-methylaminoethyl) carbonate (8.51 g, 0.022 mol) and collidine (5.91 g, 0.049 mol) in 15 cc of o-dichlorobenzene was refluxed for 75 minutes. The solvent and excess collidine were removed in vacuo and the dark red residue was passed through a silica gel plug (ethyl acetate as eluant). Evaporation of the eluate followed by vacuum distillation of the remaining oil afforded a fraction of bp ca. 170°–180° C. at 0.6 mm (1.59 g, 23% yield) identified as the title di-VOC product.

IR (μ): 5.70 (s), 5.78 (vs), 6.06 (m); CCl$_4$.

$^1$H NMR (δ): 7.00 (d of d, j=14, 6), 4.9–3.8 (m with t of j=5 at 4.14), 3.46 (broad t, j=5), 2.95 (broad s); ratio 2:8:4:6; CCl$_4$.

MS (m/e): 316 (P, 0.1%), 273.1081 (P—OCH=CH$_2$, 6%, Calc. 273.1087), 172 (4%), 128 (100%), 102 (60%).

EXAMPLE 37

Preparation of N,N'-Di-(Isobutenyloxycarbonyl)dibenzo-1,4-dioxa-8,12-diaza-cyclopentadeca-5,14-diene (a) Preparation of N,N'-di-(α-chloroisobutyloxycarbonyl)dibenzo-1,4-dioxa-8,12-diaza-cyclopentadeca-5,14-diene.

A solution of α-chloroisobutyl chloroformate (0.68 g, 3.98 mmol) in 7 cc of dichloromethane was added over 10 minutes to a cooled (0° C.), stirred solution of dibenzo-1,4-dioxa-8,12-diaza-cyclopentadeca-5,14-diene (from Fluka, 0.48 g, 1.54 mmol) and pyridine (0.26 g, 3.29 mmol) in 7 cc of dichloromethane. After stirring overnight at room temperature, the yellow reaction mixture was poured onto a silica gel plug and eluted with ethyl acetate. The eluate was rotoevaporated and the residue was dried in vacuo giving the product as a white powder; 0.84 g (94% yield) which liquified at 54°–58° C.

IR (μ): 5.85 (vs), 6.29 (w), 7.07 (vs); CH$_2$Cl$_2$.

$^1$H NMR (δ): 7.6–6.7 (m), 6.5–6.2 (m), 4.56 (s), 4.40 (s), 3.5–2.9 (m), 2.5–0.7 (m with d of J=6 at 1.05); ratio 8:2:4:4:4:16; CDCl$_3$.

(b) Preparation of N,N'-Di-(isobutenyloxycarbonyl)-dibenzo-1,4-dioxa-8,12-diaza-cyclopentadeca-5,14-diene.

A mixture of the product from Example 37a (0.75 g, 1.29 mmol), tetrabutylammonium bromide (0.057 g, 0.18 mmol), and collidine (0.52 g, 4.29 mmol) in 1.1 cc of tetrachloroethylene was refluxed for 4 hours. The solvent and excess collidine were removed under vacuum from the reaction mixture at 100° C. and the residue which remained was diluted with dichloromethane and passed through a silica gel plug using ethyl acetate as the eluant. Rotoevaporation of the eluate followed by drying in vacuo afforded the title product as a light yellow gum; 0.64 g, 98% yield.

IR (μ): 5.88 (vs), 6.92 (s); CH$_2$Cl$_2$.

$^1$H NMR (δ): 7.5–6.5 (m), 4.51 (s), 4.32 (s), 3.4–2.9 (m), 2.5–1.4 (m with broad s at 1.58); ratio 10:4:4:4:14; CDCl$_3$.

The final product from Example 37b has the structure drawn below:

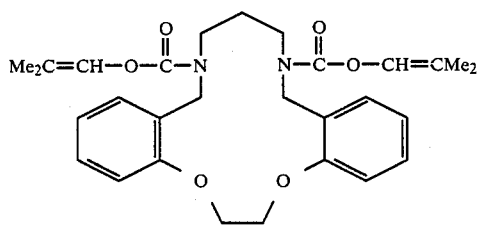

In a similar manner, dibenzo-1,4-dioxa-8,12-diaza-cyclopentadeca-5,14-diene was reacted with α-chloroethyl chloroformate (ACE-Cl) to give the intermediate N,N'-di-α-chloroethyl compound which was dehydrohalogenated as in Example 21b to give di-vinyloxycarbonyl dibenzo-1,4-dioxa-8,12-diaza-cyclopentadeca-5,14-diene.

What is claimed is:

1. A process for the preparation of vinyl carbamates of formula I

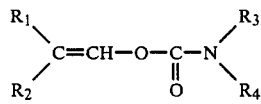 (I)

in which R$_1$ and R$_2$ are the same or different and are:
(1) hydrogen;
(2) alkyl of 1 to 6 carbon atoms which is unsubstituted or substituted by halogen atoms;
(3) or R$_1$ and R$_2$ together with the carbon atom to which they are attached form a saturated or unsaturated, 6-carbon atom ring;

R$_3$ and R$_4$ are the same or different and are:
(a) hydrogen;
(b) a C$_1$–C$_4$ alkyl which is unsubstituted or substituted by halogen or cyclohexyl;
(c) one of R$_3$ or R$_4$ is —(CH$_2$)$_3$N$^+$(CH$_3$)$_3$Cl$^-$
(d) a radical of formula

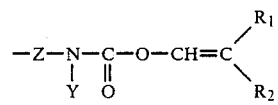

wherein Z=a chain with 2 to 6 carbon atoms, Y=C$_1$–C$_2$ alkyl, and R$_1$ and R$_2$ are as defined hereinabove, or Z is —(CH$_2$)$_2$—OCOO(CH$_2$)$_2$—

(e) phenyl which is unsubstituted or substituted by chlorine;
(f) R$_3$ and R$_4$ form together with the nitrogen atom to which they are attached a 5 or 6 member heterocyclic ring which is a piperidine, piperazine, benzotriazole, morpholine or guvacoline ring;
(g) R$_3$ and R$_4$ together with the N atom to which they are attached form a lower N'-alkyl piperazine;
(h) R$_3$ and R$_4$ together with the N atom to which they are attached form the noroxycodone or nortropine radical; or
(i) R$_3$ and R$_4$ form with the nitrogen atom to which they are attached a 1,10-diaza, 18-crown-6 ring; or
(j) when R$_3$ and R$_4$ together with the N atom to which they are attached form the piperazine or the 1,10-diaza-18-crown -6 ring, both nitrogen atoms of the ring have attached said group of formula

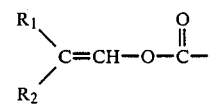

which consists of heating an α-halogenocarbamate of formula II:

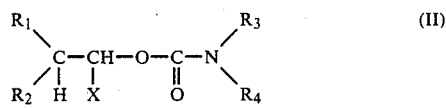 (II)

in which R$_1$, R$_2$, R$_3$ and R$_4$ have the same meaning as defined hereinabove and X is chlorine or bromine, and when in said compound of formula I R$_3$ and R$_4$ are a radical which contains a vinyl carbamate group, the latter is present in said compound of formula II in the form of a saturated carbamate containing a hydrogen atom in the β position and X in the α position, at a temperature between 80° C. and 200° C. for a period of time between several minutes up to several hours, in the presence of a catalyst, which is an easily ionizable salt, the anion of which is an halide, ClO$_4^-$ or NO$_3^-$ and the cation is a member selected from the group consisting of (a) Li$^+$, Na$^+$, K$^+$, Ca$^{++}$, (b) the metallic cation defined in (a) complexed with a crown ether, (c) the metallic cation defined in (a) complexed with a cryptand (d) an unsubstituted ammonium cation, and (e) the ammonium cation substituted by at least one radical containing 1 to 7 carbon atoms, the catalyst being added in an amount between 0.02 and 0.5 equivalents with respect to each carbamate group in said compound of formula II, under anhydrous conditions, whereby a halohydric acid which is HCl or HBr is formed and isolating said carbamate of formula (I) from the reaction mixture.

2. The process according to claim 1 wherein the onium cation is tetra-n-butylammonium cation.

3. The process according to claim 1 which is carried out in the presence of a weakly nucleophilic halohydric acid acceptor which is a member selected from the group consisting of
   (1) 2,4-dialkylpyridines and 2,4,6-trialkypyridines,
   (2) N,N-dialkylanilines, which are unsubstituted or substituted in the ring by at least one electrophilic group,
   (3) alkenes,
   (4) diisocyanates which are aliphatic diiosocyanates of formula $O{=}C{=}N{=}(CH_2)_x\text{-}N{=}C{=}O$, wherein x is between 6 and 36, or aromatic diisocyanates.

4. The process according to claim 1 which is carried out in the presence of a catalyst which is a quaternary ammonium salt or potassium chloride complexed with a crown ether and a solvent which is a halogenated benzene, triglyme or tetrachloroethylene.

5. The process according to claim 3 which is carried out in the presence of a halogenated benzene, tetrachloroethylene as a solvent and 2,4,6-collidine or β-pinene as the hydrogen acceptor.

6. The process according to claim 3 which is carried out in the presence of a catalyst which is a quaternary ammonium salt, an halohydric acid acceptor which is 2,4,6-collidine and a solvent which is tetrachloroethylene, trichloroethylene, chlorobenzene or bromobenzene.

7. The process according to claim 3 wherein the reaction is carried out in an aprotic solvent which is a member selected from the group consisting of ethers, sulfones, N,N-dialkylsulfonamides N,N,N',N' -tetraalkylsulfonylureas, halogenated aromatic hydrocarbons, dichloroethane, trichloro- or tetrachloroethylene.

* * * * *